US010480037B2

(12) United States Patent
Haddad

(10) Patent No.: US 10,480,037 B2
(45) Date of Patent: Nov. 19, 2019

(54) METHODS AND SYSTEMS FOR PREDICTING HIV-1 CORECEPTOR TROPISM

(71) Applicant: Laboratory Corporation of America Holdings, Burlington, NC (US)

(72) Inventor: Mojgan Haddad, Orinda, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 13/625,844

(22) Filed: Sep. 24, 2012

(65) Prior Publication Data

US 2013/0079233 A1 Mar. 28, 2013

Related U.S. Application Data

(60) Provisional application No. 61/538,791, filed on Sep. 23, 2011.

(51) Int. Cl.
| | | |
|---|---|---|
| *C12Q 1/70* | (2006.01) | |
| *G16B 20/00* | (2019.01) | |
| *G16B 30/00* | (2019.01) | |
| *G16B 40/00* | (2019.01) | |

(52) U.S. Cl.
CPC ............. *C12Q 1/703* (2013.01); *G16B 20/00* (2019.02); *G16B 30/00* (2019.02); *G16B 40/00* (2019.02)

(58) Field of Classification Search
None
See application file for complete search history.

(56) References Cited

U.S. PATENT DOCUMENTS

| | | |
|---|---|---|
| 5,436,131 A | 7/1995 | Condra |
| 5,837,464 A | 11/1998 | Capon |
| 6,103,462 A | 8/2000 | Paulous |
| 6,242,187 B1 | 6/2001 | Capon |
| 7,384,734 B2 | 6/2008 | Parkin |
| 7,993,824 B2 | 8/2011 | Chappey |
| 8,114,585 B2 | 2/2012 | Huang |

FOREIGN PATENT DOCUMENTS

WO    WO 99/67427    12/1999

OTHER PUBLICATIONS

Briggs, "Envelope V3 amino acid sequence predicts HIV-1 phenotype (co-receptor usage and tropism for macrophages)," AIDS, vol. 14, pp. 2937-2939, 2000.*
Altmann, "Improved prediction of response to antiretroviral combination therapy using the genetic barrier to drug resistance," Antiviral Therapy, vol. 12, pp. 169-178, 2007.*
Reeves, "Emerging Drug Targets for Antiretroviral Therapy," Drugs, vol. 65, pp. 1747-1766, 2005.*
Vandekerckhove, "European guidelines on the clinical management of HIV-1 tropism testing," Lancet Infect. Dis., vol. 11, pp. 394-407, Mar. 2011.*
Prosperi, "'Common law' applied to treatment decisions for drug resistant HIV," abstract in XIV International HIV Drug Resistance Workshop, Antiviral Therapy, vol. 10, p. S62, 2005.*
Seal, "Characterization of Newcastle Disease Virus Isolates by Reverse Transcription PCR Coupled to Direct Nucleotide Sequencing and Development of Sequence Database for Pathotype Prediction and Molecular Epidemiological Analysis," J. Clinical Microbiology, vol. 33, pp. 2624-2630, 1995.*
Altschul, S. et al., Basic Local Alignment Search Tool, J. Mol. Biol., 1990, 215:403-10.
Altschul, S. et al., Gapped BLAST and PSI-BLAST: a new generation of protein database search programs, Nucleic Acids Res., 1997, 25:3389-3402.
Ausubel et al., Current Protocols in Molecular Biology, Greene Publishing Associates and Wiley Interscience, NY, 1989.
Bennett, D. et al., Drug Resistance Mutations for Surveillance of Transmitted HIV-1 Drug-Resistance: 2009 Update, PLoS One, 2009, 4(3):e4724.
Bonhoeffer S. et al., Evidence for Positive Epistasis in HIV-1, 2004, 306:1547-50.
Briggs, D.R. et al., Envelope V3 amino acid sequence predicts HIV-1 phenotype (co-receptor usage and tropism for macrophages)., AIDS, 2000, 14(18):2937-9.
Clavel and Hance, HIV Drug Resistance, 2004, N. Engl. J. Med., 350:1023-35.
Clercq, E., Anti-HIV drugs: 25 compounds approved within 25 years after the discovery of HIV, Int. J. Antimicrob. Agents, 2009, 33:307-320.
De Jong, J. et al., Minimal Requirements for the Human Immunodeficiency Virus Type 1 V3 Domain to Support th Syncytium-Inducing Phenotype: Analysis by Single Amino Acid Substitution, J. Virol., 1992, 66(11):6777-6780.
Deng et al., Identification of a major co-receptor for primary isolates of HIV-1, 1996 Nature 381(6584):661-66.
Eddy, S.R., Multiple alignment using hidden Markov models, Proc. Int. Conf. Intell. Syst. Mol. Biol., 1995, 3:114-20.
Eddy, S.R., Hidden Markov models, Curr. Opin. Struct. Biol., 1996, 6(3):361-65.
Eddy, S.R., Profile hidden Markov models, Bioinformatics Review, 1998, 14(9):755-763.
Eisenberg, E. et al., Analysis of Membrane and Surface Protein Sequences with the Hydrophobic Moment Plot, J. Mol. Biol., 1984, 179:125-142.
Gervaix, A. et al., A new reporter cell line to monitor HIV infection and drug susceptibility in vitro, Proc. Natl. Acad. Sci. USA, 1997, 94:4653-4658.

(Continued)

*Primary Examiner* — G Steven Vanni
(74) *Attorney, Agent, or Firm* — Kilpatrick Townsend & Stockton LLP

(57) ABSTRACT

The present methods for predicting coreceptor tropism may include obtaining the amino acid and/or nucleic acid sequence of at least a portion of the envelope or envelope coding region from a biological sample obtained from a subject; analyzing the amino acid sequence, nucleic acid sequence, or both of the portion of the envelope or envelope coding region using a case based reasoning analysis; and determining the coreceptor tropism. Also described are systems and computer readable media for utilizing the systems or performing the methods.

19 Claims, 10 Drawing Sheets

(56) References Cited

OTHER PUBLICATIONS

Goetz et al., Relationship between HIV Co-Receptor Tropism and Disease Progression in Persons with Untreated Chronic HIV Infection, 2009, J. Acquired Immune Defic. Syndr., 50(3):259-66.
Haddad et al., Feasibility analysis of a case-based reasoning system for automated detection of coronary heart disease from myocardial scintigrams, 1997, Artif. Intell. Med., 9(1):61-78.
Jensen, M.A. et al., Improved Coreceptor Usage Prediction and Genotypic Monitoring of R5-to-X4 Transition by Motif Analysis of Human Immunodeficiency Virus Type 1 env V3 Loop Sequences, J. Virol., 2003, 77(24):13376-13388.
Jensen, M.A. and Van 'T Wout, A.B., Predicting HIV-1 Corecptor Usage with Sequence Analysis, AIDS Rev., 2003, 5(2):104-12.
Johnson, V.A. et al., Update of the Drug Resistance Mutations in HIV-1: Dec. 2008, Topics in HIV Med., 2008, 16:138-45.
Kolodner, J.L. et al., 1989, The mediator: a case study of a case-based problem solver, 106.
Kolodner, J. 1993, Case-Based Reasoning, 668.
Low, A.J. et al., Current V3 genotyping alogorithms are inadequate for predicting X4 co-receptor usage in clinical isolates, AIDS, 2007, 21(14):F17-24.
Masso, M. and Vaisman, I., Accurate and efficient gp120 V3 loop structure based models for the determination of HIV-1 co-receptor usage, BMC Bioinformatics, 2010, 11:494.
Messing, J. et al., A system for shotgun DNA sequencing, Nuc. Acids Res., 1981, 9:309.
Petropoulos, C.J. et al., A Novel Phenotypic Drug Susceptibility Assay for Human Immunodeficiency Virus Type 1, Antimicob. Agents Chemother., 2000, 44(4):920-928.
Pillai, S. et al., A New Perspective on V3 Phenotype Prediction, AIDS Res. Hum. Retrovir., 2003, 19(2):145-49.
Race, E. et al., Analysis of HIV cross-resistance to protease inhibitors using a rapid single-cyle recombinant virus assay for patients failing on combination therapies, AIDS, 1999, 13:2061-2068.
Resch, W. et al., Improved Success of Phenotype Prediction of the Human Immunodeficiency Virus Type 1 from Envelope Variable Loop 3 Sequence Using Neural Networks, Virology, 2001, 288(1):51-62.
Reynes, J. et al., TORO: Ninety-Six-Week Virologic and Immunologic Response and Safety Evaluation of Enfuvirtide with an Optimized Background of Antiretrovirals, AIDS Patient Care STDS, 2007, 21(8):533-43.
Rhee, S. et al., Distribution of Human Immunodeficiency Virus Type 1 Protease and Reverse Transcriptase Mutation Patterns in 4,183 Persons Undergoing Genotypic Resistance Testing, Antimicrob. Agents and Chemo., 2004, 48(8):3122-3126.
Rice, P. et al., EMBOSS: The European Molecular Biology Open Software Suite, Trends Genet., 2000, 16(6):276-77.
Richman, D.D., Nailing down another HIV target, Nature Med., 1998, 4(11):1232-1233.
Russell, W.L., Factors Affecting Mutagenicity of Ethylnitrosourea in the Mouse Specific-Locus Test and Their Bearing on Risk Estimation, In Environmental Mutagens and Carcinogens: Proceedings of the Third International Conference on Environmental Mutagens, Tokyo, Mishima and Kyoto, 1982.
Russell, W. et al., Specific-locus test shows ethylnitrosourea to be the most potent mutagen in the mouse., Proc. Nat. Acad. Sci. USA, 1979, 76(11):5818-5819.
Sambrook, J. et al., 2001, Molecular Cloning: A Laboratory Manual, Cold Spring Harbor Laboratory, 3rd ed., NY.
Sanger, F. et at., DNA sequencing with chain-terminating inhibitors, Proc. Natl. Acad. Sci. USA, 1977, 74(12):5463-5467.
Sarkar G. and Sommer, S.S., The "Megaprimer" Method of Site-Directed Mutagenesis, Biotechniques, 1990, 8(4):404-407.
Schank, R.C., Dynamic Memory: A Theory of Learning in Computers and People, 1982.
Shafer, R.W. and Schapiro, J.M., HIV-1 Drug Resistance Mutations: an Updated Framework for the Second Decade of HAART, AIDS Rev., 2008, 10:67-84.

\* cited by examiner

FIGURE 5
FIG. 5A
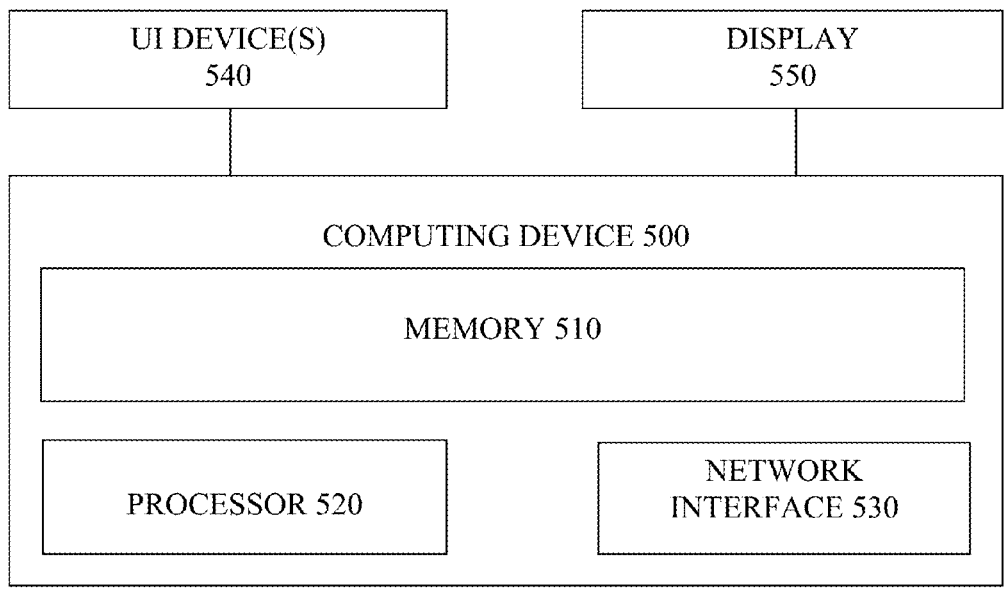
FIG. 5B
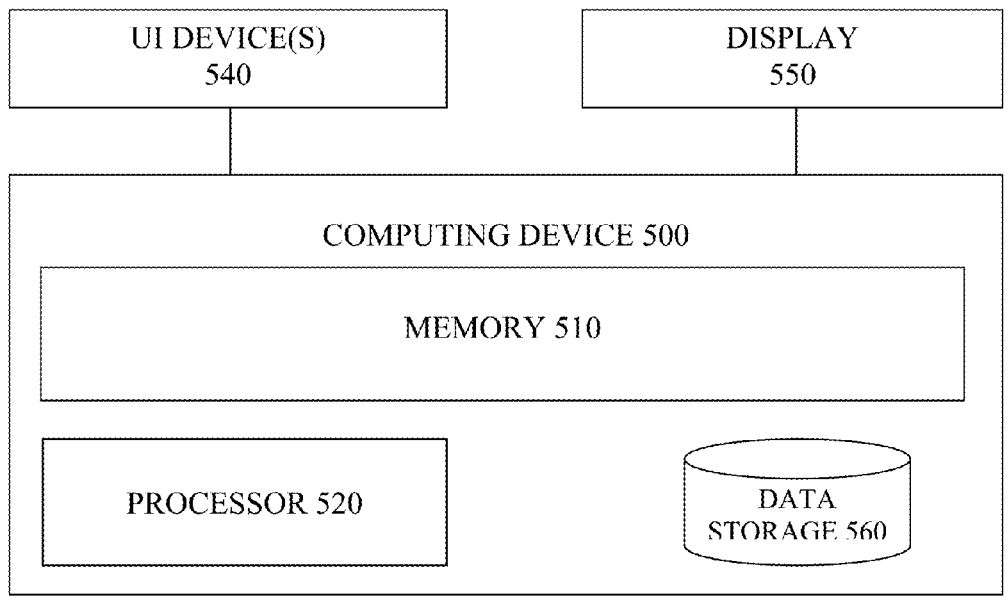

METHODS AND SYSTEMS FOR PREDICTING HIV-1 CORECEPTOR TROPISM

CROSS REFERENCE TO RELATED APPLICATIONS

This application claims priority to U.S. Provisional Application No. 61/538,791, which was filed Sep. 23, 2011. The entire contents of that application are incorporated herein by reference.

FIELD OF THE INVENTION

The invention relates to methods for predicting coreceptor tropism of a virus. The invention further relates to systems and computer-readable media for performing methods for predicting coreceptor tropism. In particular embodiments, the effects of certain viral genotypes are used for predicting coreceptor tropism using a case based reasoning analysis.

BACKGROUND

Enveloped animal viruses attach to and enter their host cells via the interaction of certain viral proteins located in the virion membrane (envelope proteins) and host cell surface proteins (receptors and coreceptors for the virus). Receptor recognition and binding are mediated by the virus's envelope protein. Human Immunodeficiency Virus type 1 (HIV-1) gains entry into the human host cell by using CD4 and either CXCR4 (X4) or CCR5 (R5) coreceptors (Deng et al., 1996, Nature 381(6584):661-66). Virus entry is an attractive target for anti-viral treatment, and numerous drugs designed to block virus attachment or membrane fusion have been or are currently being evaluated in pre-clinical or clinical studies for HIV treatment (See, e.g., Richman, 1998, Nature Med., 4:1232-1233; PhRMA, 1999, "New Medicines in Development for AIDS," Pharmaceutical Research and Manufacturers of America; Stephenson, 1999, JAMA, 282:1994). Some examples of entry inhibitors that have been or are being investigated include attachment inhibitor SCH-D (vivriviroc, which blocks the interaction between viral membrane proteins of HIV-1 and the cellular coreceptor CCR5, Schering-Plough), UK-427857 (maraviroc; Pfizer), TNX-355 (Tanox Inc.), AMD-070 (AnorMED), Pro 140 (Progenics), FP-21399 (EMD Lexigen), BMS-488043 (Bristol-Myers Squibb), and T-20 (enfuvirtide; Roche/Trimeris).

The effectiveness of the currently available drugs for treatment of HIV, however, varies from subject to subject depending, at least in part, on genetically-controlled susceptibility to each drug. Over 200 mutations have been identified as being associated with reduced susceptibility to one or more of the approved drugs (Clercq, 2009, Int. J. Antimicrob. Agents 33:307-20; Shafer and Schapiro, 2008, AIDS Rev. 10:67-84; Clavel and Hance, 2004, N. Engl. J. Med. 350:1023-35; Johnson, 2008, Topics in HIV Med. 16:138-45; Bennett, 2009, PLoS ONE 4:e4724). Due to the complexity of the treatment options available and the many resistance (reduced susceptibility) associated mutations, it is increasingly difficult to develop a comprehensive understanding of HIV drug resistance. Resistance mutations differ in their potency to resist drug pressure, in their degree of cross-resistance to different drugs or drug classes, and in the fitness costs induced in the absence of treatment. Moreover, their effects depend to varying degree on the context of accompanying mutations (Rhee et al., 2004, Antimicrob. Agents and Chemo. 48:31226; Bonhoeffer et al., 2004, Science 306:154750).

Drug resistance testing for individuals infected with HIV-1 is a key component of the management of antiretroviral therapy in North America and Europe. And in particular, accurate coreceptor tropism (CRT) determination is critical when making treatment decisions in HIV management. Assays for assessment of drug susceptibility are based on the sequencing of a patient's virus (genotyping), on virus replication inhibition in vitro (phenotyping), or both.

The HIV-1 envelope glycoprotein gp120 contains five highly variable regions or loops, designated V1 through V5, that are separated by four relatively "constant" regions (C1-C4). The first four variable regions form loops through intramolecular disulfide bonds. These variable regions are thought to cover a significant portion of the exposed surface on the trimeric gp120 complex. Gp120 has significant sequence variation, which may arise through recombination and point mutation, as well as by insertion and deletion of one or more nucleotides. The V1/V2 region and the V3 loop of the envelope protein are targets for neutralizing antibodies, and the V3 loop largely determines whether a virus uses R5, X4, or either coreceptor to infect its host cells. Given the use of entry inhibitors as a treatment option, it is critical to have diagnostic assays available that quickly and accurately determine the dominant coreceptor tropism in a clinical setting.

The variability of the amino acid sequence of the third hypervariable (V3) loop is shown in FIG. 1. Genotype based in silico prediction of virus tropism utilizing the sequence of the V3 loop of the envelope protein offers a rapid test for coreceptor usage. To date, many bioinformatics methods for tropism prediction have been developed and tested. These bioinformatics predictors include support vector machines (SVM) (Pillai et al., 2003, AIDS Res. Hum. Retrovir. 19(2):145-49; Sing et al., 2007, Antirviral Therapy 12(7): 1097-1106), neural networks (NN) (Resch et al., 2001, Virology 288(1):51-62), decision trees (Masso and Vaisman, BMC Bioinformatics 11:494), position specific scoring matrices (PSSM) (Jenesen et al., 2003, J. Virol. 77(24): 13376-88), multiple linear regression (Briggs et al., 2000, AIDS 14(18):2937-39), and the 11/25 rule (De Jong et al., 1992, J. Virol. 66(11):6777-80). However, many of these methods were trained on clonal sequences, and may not be adequate for tropism testing of clinical isolates that are often heterogeneous and have high level of sequence ambiguity (Low et al., 2007, AIDS 21(14):F17-24). Moreover, these methods generally are developed by fitting a model into the respective training set, and often do not perform as well with independent or unseen datasets (Jensen et al., 2003, AIDS Rev. 5(2):104-12).

What is needed, therefore, are efficient and accurate diagnostic assays and methods that can be used to quickly and accurately determine the dominant coreceptor tropism for a particular virus or population of viruses in order to guide patient treatment. Systems and computer readable media for use in such assays and methods are also needed.

SUMMARY OF THE INVENTION

In at least one aspect, the invention provides methods for predicting the tropism of a virus, including obtaining an amino acid sequence, nucleic acid sequence, or both, of at least one portion of an envelope or envelope coding region of a virus from a biological sample obtained from a subject; analyzing the amino acid sequence, nucleic acid sequence, or both, of the at least one portion of the envelope or envelope coding region to sequence data stored in a database, wherein the comparing uses a case based reasoning (CBR) analysis, and wherein the data includes a plurality of sequences for the portion of the envelope or envelope coding region from viruses for which the tropism has been evaluated; and determining the tropism of the virus from the biological sample. In some embodiments, the virus is human immunodeficiency virus 1 (HIV-1). In some embodiments of the methods, the at least one portion of the envelope or envelope coding region includes the variable region 3 (V3) loop or coding region. In certain embodiments, the subject has been treated with a viral entry inhibitor. The viral entry inhibitor may be, but is not limited to, PRO 542, TNX-355, mAb B12, mAb B4, BMS-488-403, UK-427857, SCH-D, GW-873140, AMD-3100, AMD-11070, TAK-220, TB-652, INCB9471, HGSI-004 Pro-140, mAb004, KRH-3140, and KRH-3955. In some embodiments, the data comprises a plurality of sequences from viruses of the same subtype as the virus from the biological sample. In certain embodiments, the methods also include determining sequence characteristics of the amino acid sequence or nucleic acid sequence of the at least one portion of the envelope or envelope coding region, wherein the sequence characteristics are nucleotide or amino acid mixtures, molecular weight, net charge, isoelectric point, molar composition, profile Hidden Markov Model (pHMM) values, or a combination thereof; and analyzing the sequence characteristics of the at least one portion of the envelope or envelope coding region to sequence characteristics stored in a database, wherein the comparing uses a case based reasoning (CBR) analysis, and wherein the data includes a plurality of sequence characteristics from viruses for which the tropism has been evaluated.

In another aspect, the invention provides a system including a computer readable medium; and a processor in communication with the computer readable medium, the processor configured to receive sequence data, the sequence data representing an amino acid and/or nucleic acid sequence of at least a portion of an envelope or envelope coding region of a virus from a biological sample obtained from a subject; access other sequence data from viruses for which tropism has been evaluated; compare the received sequence data to the other sequence data; determine whether there is at least one sequence feature in the received sequence data; and in response to a determination that there is the at least one sequence feature in the received sequence data, determine the tropism of the virus from the biological sample using a case based reasoning analysis.

In another aspect, the invention provides a computer readable medium containing program code including program code for receiving sequence data, the sequence data representing an amino acid sequence, nucleic acid sequence, or both of at least a portion of an envelope or envelope coding region of a virus from a biological sample obtained from a subject; program code for accessing other sequence data from viruses for which tropism has been evaluated; program code for comparing the received sequence data to the other sequence data; program code for determining whether there is at least one sequence feature in the received sequence data; and program code for, in response to a determination that there is the at least one sequence feature in the received sequence data, determining the tropism of the virus from the biological sample using a case based reasoning analysis.

In another aspect, the invention provides a method to develop a model for predicting tropism including: building a case library by obtaining an amino acid sequence, nucleic acid sequence, or both, of at least one portion of an envelope or envelope coding region from a plurality of viruses of different subtypes and different treatment history; determining sequence characteristics of the amino acid sequence, nucleic acid sequence, or both of the at least one portion of the envelope or envelope coding region, wherein the sequence characteristics are nucleotide or amino acid mixtures, molecular weight, net charge, isoelectric point, molar composition, profile Hidden Markov Model (pHMM) values, or a combination thereof; determining the tropism of the plurality of viruses; selecting features and sequence characteristics that correlate with tropism determination for performing the similarity assessment; assigning weights to each selected feature and sequence characteristic based on the significance of the correlation with tropism determination; and generating a process for making a tropism call based on the selected features and sequence characteristics.

Further aspects of the invention, and further embodiments of each of the above aspects, are described in greater detail below.

BRIEF DESCRIPTION OF THE FIGURES

Non-limiting embodiments of the methods and systems of the invention are exemplified in the following figures. These figures are included as part of the description of the invention. These figures are intended to illustrate certain embodiments of the claimed inventions, but are not intended to limit the scope of the claimed inventions in any way.

FIGS. 5A and 5B show block diagrams depicting exemplary computing devices according to various embodiments.

FIGS. 6A through 6P are graphs showing the distribution of nucleotide and amino acid ambiguities in the V3 loop coding region, grouped by tropism as determined by ENHANCED SENSITIVITY TROFILE ASSAY (ESTA, Monogram Biosciences, South San Francisco, Calif.). AA refers to amino acid ambiguity, and LEN refers to sequence length. All other letters correspond to the IUPAC single letter amino acid codes. B represents aspartic acid or asparagine residues; X represents any amino acid residue; and Z represents glutamic acid or glutamine residues. The x axis shows viruses that were R5, X4, or dual/mixed tropic. The y axis in FIGS. 6A and 6B represents the length in nucleotides or amino acids, respectively. In FIGS. 6C-6M, the y axis represents the number of nucleotide positions within the V3 region that were called that nucleotide within the training set's sequences. In FIGS. 6N-6P, the y axis represents the number of amino acid positions that were called that amino acid within the training set's sequences.

FIG. 10A represents calls of X4 using viruses (X4 or DM tropic), and FIG. 10B represents R5 tropic viruses. The number 24 in FIG. 10A is the number of X4/DM viruses, and the number 15 in FIG. 10B is the number of R5 tropic viruses as determined by the TROFILE ES assay (ESTA).

DETAILED DESCRIPTION

Figure 1:
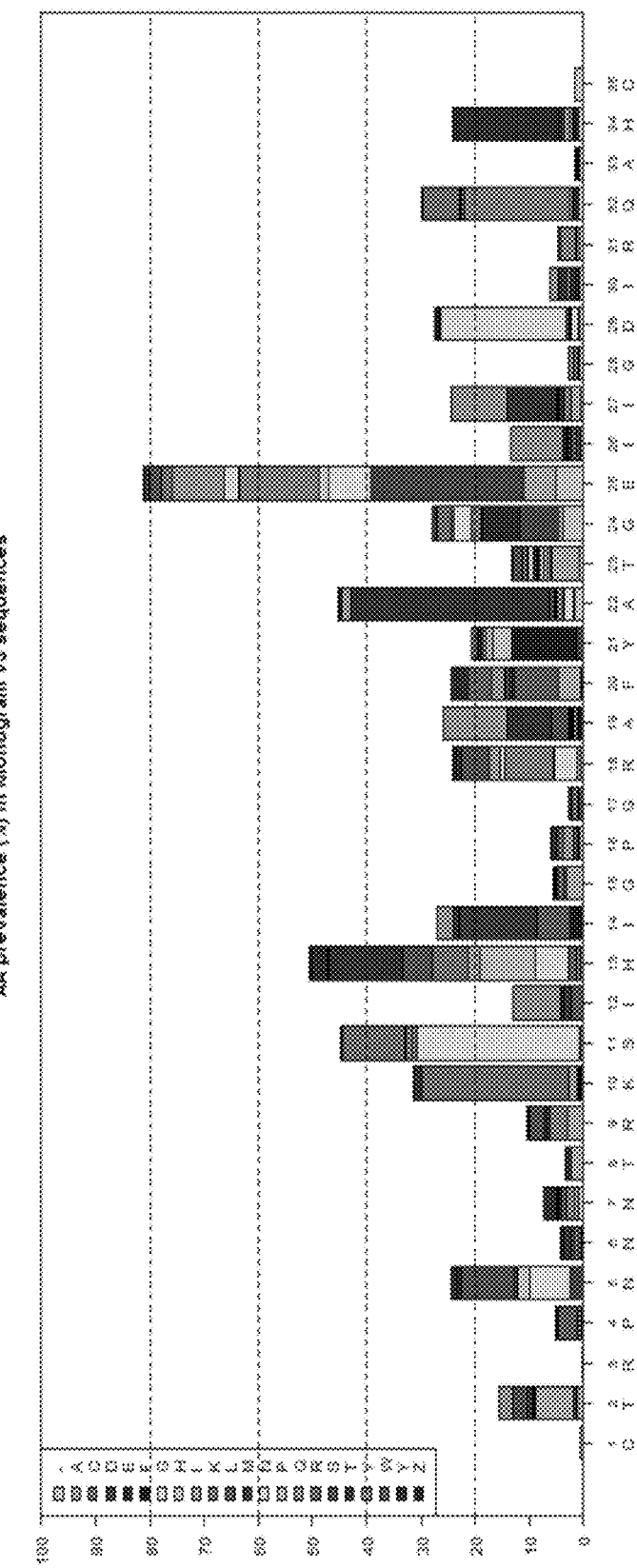
FIG. 1 is a graph showing the prevalence of each amino acid residue in the V3 loop coding region sequences in the 835 samples in the dataset that were characterized. The letters shown are the standard IUPAC single letter amino acid codes. Z represents glutamic acid or glutamine residues. The y axis shows the percentage of the amino acid residue present. The x axis indicates the position number in the V3 loop sequence, as well as the amino acid present in the subtype B consensus V3 loop sequence.

The following paragraphs provide a description of various embodiments of the invention. Such embodiments are intended to describe methods and systems that are included within the scope of the invention, but are not intended to serve as a limit to the scope of the claimed subject matter. The claims shall determine the scope of the invention.

Definition and Abbreviations

The following definitions and abbreviations are provided for convenience. The application may use various terms and phrases, including technical terms and phrases, which are not expressly defined herein. When a term or phrase is not expressly defined, the term or phrase shall have the meaning that such term or phrase would have to the person of ordinary skill in the art in the field(s) to which the invention is directed.

As used herein, the term "tropism" or "coreceptor tropism" is defined as the ability of a virus (e.g., HIV-1) to infect a target cell using a specific coreceptor. HIV-1 viruses or virus populations that can use only the CCR5 chemokine coreceptor to infect $CD4^+$ cells are "R5 tropic." "X4 tropic" viruses or virus populations can use only the CXCR4 chemokine coreceptor to infect $CD4^+$ cells. "Dual tropic" or "D-tropic" viruses or virus populations can use either the CCR5 or CXCR4 coreceptors to infect $CD4^+$ cells. "Mixed tropic" or "M-tropic" virus populations may contain various combinations of R5 viruses, X4 viruses, and/or dual-tropic viruses.

As used herein, a "case-based reasoning" (CBR) analysis is a technique that solves new problems based on the solutions to similar past problems. CBR originated in the early eighties and was quickly adopted into a wide range of disciplines, from solving routine resource disputes as implemented in MEDIATOR to assisting with medical diagnoses (Kolodner et al., 1993, Case-Based Reasoning, 668; Schank, 1982, Dynamic Memory: A Theory of Learning in Computers and People; Kolodner et al., 1988, The mediator: a case study of a case-based problem solver, 106; Haddad, 1997, Artif. Intell. Med. 9(1):61-78). A case-based reasoner solves new problems with an unknown solution by adapting solutions that have been demonstrated to solve previous problems. Steps to build a case-based reasoning tool consists of: 1) building a case library of problems with their solution from cases that are a representative set of the population; 2) defining a similarity metric so that a similarity assessment between the problem at hand and the cases stored in the case library can be made; and 3) setting a selection and adaptation strategy for making a prediction on the basis of found similar cases.

A "genotypic assay" is an assay that determines a genotype or sequence of an organism, a part of an organism, a population of organisms, a coding region, a part of a coding region, a population of coding regions, a gene, a part of a gene, or a population of genes. Typically, a genotypic assay involves determination of the nucleic acid sequence of the relevant coding region or coding regions. Such assays are frequently performed in HIV to establish, for example, whether certain mutations are associated with drug resistance or susceptibility or altered replication capacity are present.

As used herein, "genotypic data" are data about the genotype of, for example, a virus. Examples of genotypic data include, but are not limited to, the nucleotide or amino acid sequence of a virus, a part of a virus, a viral gene, a part of a viral gene, or the identity of one or more nucleotides or amino acid residues in a viral nucleic acid or protein.

Unless noted otherwise, the standard one-letter and three-letter abbreviations for amino acids are used. When polypeptide sequences are presented as a series of one-letter and/or three-letter abbreviations, the sequences are presented in the N→C direction, in accordance with common practice. Also, where specified, individual amino acids in a sequence are represented herein as AN, wherein A is the standard one letter symbol for the amino acid in the sequence, and N is the position in the sequence. Mutations are represented herein as $A_1NA_2$, wherein $A_1$ is the standard one letter symbol for the amino acid in the reference protein sequence, $A_2$ is the standard one letter symbol for the amino acid in the mutated protein sequence, and N is the position in the amino acid sequence. For example, a G25M mutation represents a change from glycine to methionine at amino acid position 25. Mutations may also be represented herein as $NA_2$, wherein N is the position in the amino acid sequence and $A_2$ is the standard one letter symbol for the amino acid in the mutated protein sequence (e.g., 25M, for a change from the wild-type amino acid to methionine at amino acid position 25). Additionally, mutations may also be represented herein as $A_1N$, wherein $A_1$ is the standard one letter symbol for the amino acid in the reference protein sequence and N is the position in the amino acid sequence (e.g., G25 represents a change from glycine to any amino acid at amino acid position 25). This notation is typically used when the amino acid in the mutated protein sequence is either not known or, if the amino acid in the mutated protein sequence could be any amino acid, except that found in the reference protein sequence. The amino acid positions are numbered based on the full-length sequence of the protein from which the region encompassing the mutation is derived. Representations of nucleotides and point mutations in DNA sequences are analogous.

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Unless specified otherwise, single-stranded nucleic acid sequences that are represented as a series of one-letter abbreviations, and the top strand of double-stranded sequences, are presented in the 5'→3' direction.

Unless otherwise specified, "primary mutation" refers to a mutation that affects the enzyme active site (e.g., at those amino acid positions that are involved in the enzyme-substrate complex) or that reproducibly appears in an early round of replication when a virus is subject to the selective pressure of an antiviral agent, or, that has a large effect on phenotypic susceptibility to an antiviral agent. A "secondary mutation" refers to a mutation that is not a primary mutation and that contributes to reduced susceptibility or compensates for gross defects imposed by a primary mutation.

The term "% sequence homology" is used interchangeably herein with the terms "% homology," "% sequence identity," and "% identity" and refers to the level of amino acid sequence identity between two or more peptide sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. In some embodiments of the invention, levels of sequence identity include, but are not limited to, 60% or more, 70% or more, 80% or more, 85% or more, 90% or more, 95% or more, or 98% or more sequence identity to a given sequence.

Various computer programs may be used to determine identity between two sequences. Such computer programs include, but are not limited to, the suite of BLAST® (National Library of Medicine, Bethesda, Md.) programs, e.g., BLASTN, BLASTX, and TBLASTX, BLASTP and TBLASTN, publicly available on the Internet at the National Center for Biotechnology Information (NCBI) BLAST® website. See also Altschul et al., J. Mol. Biol., Vol. 215, pp. 403-10 (1990) (with special reference to the published default setting, i.e., parameters w=4, t=17) and Altschul et al., Nucleic Acids Res., Vol. 25, pp. 3389-3402 (1997). Sequence searches are typically carried out using the BLASTP program when evaluating a given amino acid sequence relative to amino acid sequences in the GenBank Protein Sequences and other public databases. The BLASTX program is suitable for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Altschul, et al. (1997).

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

The term "polar amino acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S), and Thr (T).

The term "nonpolar amino acid" refers to a hydrophobic amino acid having a side chain that is uncharged at physiological pH and which has bonds in which the pair of electrons shared in common by two atoms is generally held nearly equally by each of the two atoms (e.g., the side chain is not polar). Genetically encoded nonpolar amino acids include Ala (A), Gly (G), Ile (I), Leu (L), Met (M), and Val (V).

The term "hydrophilic amino acid" refers to an amino acid exhibiting a hydrophobicity of less than zero according to the normalized consensus hydrophobicity scale of Eisenberg et al., J. Mol. Biol., Vol. 179:125-142 (1984). Genetically encoded hydrophilic amino acids include Arg (R), Asn (N), Asp (D), Glu (E), Gln (Q), His (H), Lys (K), Ser (S), and Thr (T).

The term "hydrophobic amino acid" refers to an amino acid exhibiting a hydrophobicity of greater than zero according to the normalized consensus hydrophobicity scale of Eisenberg et al. (1984). Genetically encoded hydrophobic amino acids include Ala (A), Gly (G), Ile (I), Leu (L), Met (M), Phe (F), Pro (P), Trp (W), Tyr (Y), and Val (V).

The term "acidic amino acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

The term "basic amino acid" refers to a hydrophilic amino acid having a side chain pK value of greater than 7. Basic amino acids typically have positively charged side chains at physiological pH due to association with hydronium ion. Genetically encoded basic amino acids include Arg (R), His (H), and Lys (K).

A "mutation" is a change in an amino acid sequence or in a corresponding nucleic acid sequence relative to a reference nucleic acid or polypeptide. For embodiments of the invention comprising HIV envelope coding region, the reference nucleic acid encoding the envelope coding regions is the sequence present in HXB2 HIV. Likewise, the reference envelope polypeptide is that encoded by the HXB2 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., Methods in Enzymology, 65:499 (1980)), dideoxy sequencing (Sanger et al., Proc. Natl. Acad. Sci., 74:5463 (1977)) or hybridization-based approaches (see e.g., Sambrook et al., Molecular Cloning: A Laboratory Manual, Cold Spring Harbor Laboratory (3rd ed., 2001); and Ausubel et al., Current Protocols in Molecular Biology, Greene Publishing Associates and Wiley Interscience (1989)).

A "resistance-associated mutation" ("RAM") in a virus is a mutation correlated with reduced susceptibility of the virus to an anti-viral agent. A RAM can be found in several viruses including, but not limited to, a human immunodeficiency virus ("HIV"). Such mutations can be found in one or more of the viral proteins, for example, in the envelope protein of HIV. A RAM is defined relative to a reference strain. For embodiments of the invention comprising HIV protease, the reference envelope is the envelope encoded by HXB2 HIV.

As used herein, a "mutant" is a virus, gene, coding region, or protein having a sequence that has one or more changes relative to the sequence of a reference virus, gene, coding region, or protein. The terms "peptide," "polypeptide," and "protein" are used interchangeably throughout this application. As used herein, the terms "reference" and "wild-type" are used interchangeably. The terms "polynucleotide," "oligonucleotide," and "nucleic acid" are used interchangeably throughout this application.

As used herein, a "sequence feature" refers to the presence of a particular amino acid or nucleotide at a particular position in the protein or coding region that correlates with a particular tropism. As used herein, a "sequence characteristic" includes, but is not limited to nucleotide or amino acid mixture, molecular weight, net charge, isoelectric point, molar composition, or profile Hidden Markov Model (pHMM) values of a sequence, or a combination thereof.

A "phenotypic assay" is a test that measures the sensitivity of a virus (such as HIV) to a specific anti-viral agent.

"Susceptibility" refers to a virus's response to a particular drug. A virus that has decreased or reduced susceptibility to a drug has an increased resistance or decreased sensitivity to the drug. A virus that has increased or enhanced or greater susceptibility to a drug has an increased sensitivity or decreased resistance to the drug.

Generally, phenotypic susceptibility of a virus to a given drug is a continuum. Nonetheless, it may be practically useful to define a threshold or thresholds to simplify interpretation of a particular fold-change result. For drugs where sufficient clinical outcome data have been gathered, it is possible to define a clinical cutoff value, as below. The term "clinical cutoff value" refers to a specific point at which resistance begins and sensitivity ends. It is defined by the drug susceptibility level at which a subject's probability of treatment failure with a particular drug significantly increases. The cutoff value is different for different anti-viral agents, as determined in clinical studies. Clinical cutoff values are determined in clinical trials by evaluating resistance and outcomes data. Phenotypic drug susceptibility is measured at treatment initiation. Treatment response, such as change in viral load, is monitored at predetermined time points through the course of the treatment. The drug susceptibility is correlated with treatment response, and the clinical cutoff value is determined by resistance levels associated with treatment failure (statistical analysis of overall trial results).

The term "$IC_n$" refers to inhibitory concentration effective to inhibit "n" percentage of a microorganism in a sample. That is, it is the concentration of drug in the subject's blood or in vitro needed to suppress the reproduction of a disease-causing microorganism (such as HIV) by n %. Thus, "$IC_{50}$" refers to the concentration of an antiviral agent at which virus replication is inhibited by 50% of the level observed in the absence of the drug. The term "Subject $IC_{50}$" refers to the drug concentration required to inhibit replication of the virus from a subject by 50% and "reference $IC_{50}$" refers to the drug concentration required to inhibit replication of a reference or wild-type virus by 50%. Similarly, "$IC_{90}$" refers to the concentration of an anti-viral agent at which 90% of virus replication is inhibited. In some embodiments, a virus that has reduced susceptibility to an inhibitor demonstrates a decrease in the maximum percentage inhibition, rather than an increase in the $IC_{50}$ value.

A "fold change" is a numeric comparison of the drug susceptibility of a subject virus and a drug-sensitive reference virus. For example, the ratio of the Subject $IC_{50}$ to the drug-sensitive reference $IC_{50}$ (i.e., Subject $IC_{50}$/Reference $IC_{50}$) is a Fold Change ("FC"). A fold change of 1.0 indicates that the subject virus exhibits the same degree of drug susceptibility as the drug-sensitive reference virus. A fold change less than 1 indicates the subject virus is more sensitive than the drug-sensitive reference virus. A fold change greater than 1 indicates the subject virus is less susceptible than the drug-sensitive reference virus. A fold change equal to or greater than the clinical cutoff value means the subject virus has a lower probability of response to that drug. A fold change less than the clinical cutoff value means the subject virus is sensitive to that drug.

A virus may have an "increased likelihood of having reduced susceptibility" to an anti-viral treatment if the virus has a property, for example, a mutation, that is correlated with a reduced susceptibility to the anti-viral treatment. A property of a virus is correlated with a reduced susceptibility if a population of viruses having the property is, on average, less susceptible to the anti-viral treatment than an otherwise similar population of viruses lacking the property. Thus, the correlation between the presence of the property and reduced susceptibility need not be absolute, nor is there a requirement that the property is necessary (e.g., that the property plays a causal role in reducing susceptibility) or sufficient (e.g., that the presence of the property alone is sufficient) for conferring reduced susceptibility.

As used herein, the phrase "binding site entry inhibitors" is used to refer to inhibitors that target a host protein, and the phrase "blocking entry inhibitors" is used to refer to inhibitors that target a viral protein.

Case Based Reasoning Analysis of Envelope Coding Regions

Case Based Reasoning (CBR) analysis is particularly promising as a genotype based tropism prediction method, analyzing the sequence of viral proteins that interact with host proteins. CBR analysis may directly utilize at least a portion of the envelope coding region of clinical specimens generated through bulk or clonal sequencing in order to predict the tropism of a new sample. In some embodiments, when the virus is HIV, the portion of the envelope coding region may comprise the V3 region, V1/V2 regions, V4 region, V5 region, gp120SU (i.e., surface envelope protein), gp41TM (i.e., transmembrane envelope protein), Pgp160 (i.e., complete envelope polyprotein). In one embodiment, the portion comprises the V3 region. The instant application discloses a novel assay and method for genotypic tropism prediction utilizing a CBR method. A case library is built from selected records with matched genotype and phenotype data from ESTA. Features and sequence characteristics are selected for performing a similarity assessment. A similarity metric is defined by assigning weights to each selected feature or characteristic, and a process for making the tropism call is defined by a case selection and adaptation strategy.

In certain embodiments, a case library was generated from HIV-1 specimens for which the V3 sequence and the phenotypic tropism assessment had been determined. The amino acid sequence of the V3 region and the physiochemical characteristics of the V3 sequence highly associated with tropism were characterized. A weight was assigned to each selected feature for a similarity score assessment. A process was then implemented for retrieving relevant cases from the case library and generating a tropism prediction according to the most similar cases. Each of these steps in described in more detail below in the Examples.

Methods and Systems to Predict Effects of Coding Region Sequence

The methods and systems described herein may be applied to the analysis of coding regions from any source (e.g., biological samples obtained from humans and the like, cell culture samples, samples obtained from plants or insects).

In certain embodiments of the methods and systems of the invention, the sample may comprise a virus. In certain embodiments, the virus is an HIV-1. Also, as noted herein, the methods may be applied to either nucleic acid or amino acid sequence data. For example, in certain embodiments, the methods are used to analyze amino acid sequences in a protein. However, the methods may also be used to analyze changes in drug susceptibility that can occur as a result of mutations in non-coding regions (e.g., promoters, enhancers).

In some embodiments, where the sequence comprises a mutation, the sequence is compared to a reference sequence. For example, in some such embodiments, the reference HIV is HXB2. Methods of analyzing and characterizing genes from various samples are known in the art. See, for example, U.S. Pat. Nos. 7,384,734 and 7,993,824, which are incorporated by reference in their entireties, and specifically those portions of their specifications that refer to abbreviations, definitions, the virus, and viral samples that may be used, methods to detect the presence or absence of mutations in a virus, and methods for measuring the phenotypic susceptibility of a mutant virus.

Figure 2:
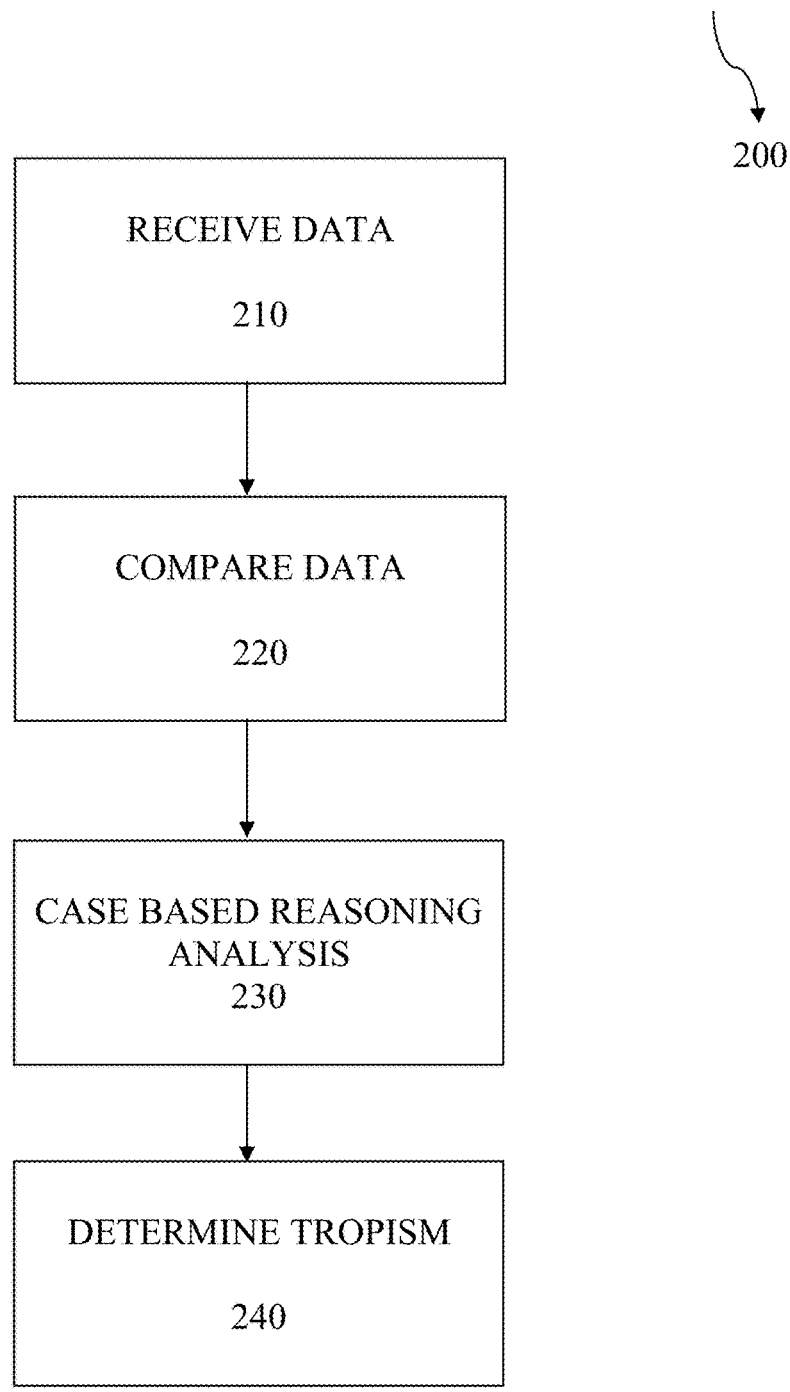
FIG. 2 shows a flow chart directed to a method for predicting coreceptor tropism according to certain embodiments.
Figure 4:
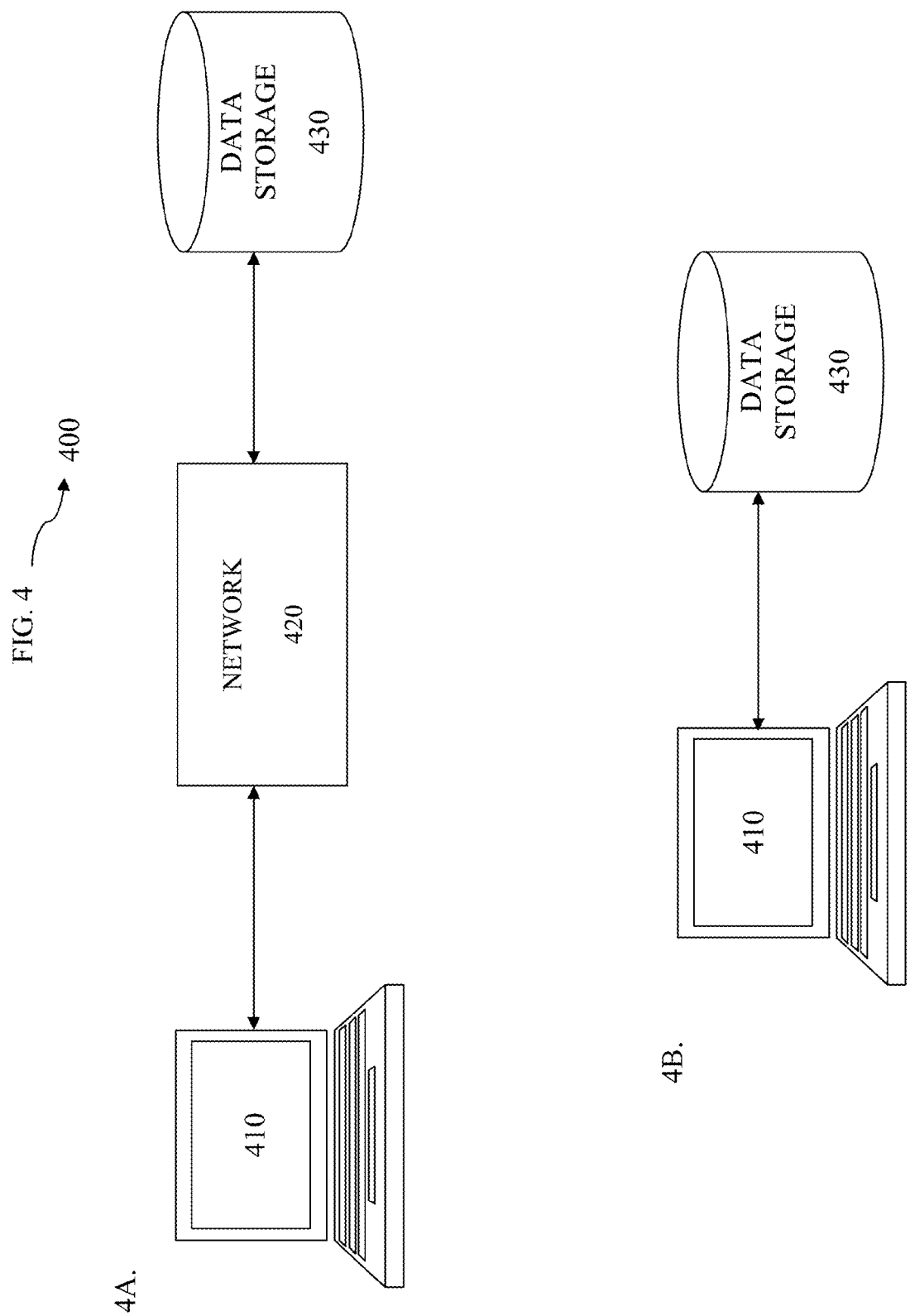
FIGS. 4A and 4B show system diagrams depicting exemplary computing devices in exemplary computing environments according to various embodiments.

FIG. 2 illustrates a flow chart directed to a system 200 of predicting the effect of at least a portion of the envelope coding region according to an embodiment of the present methods. The method 200 shown in FIG. 2 will be described with respect to the systems 400 and 401 shown in FIGS. 4A and 4B and the electronic devices 500 and 501 shown in FIGS. 5A and 5B.

In the embodiment shown in FIG. 2, the invention provides methods for predicting coreceptor tropism of a virus, the method comprising: (a) obtaining the nucleic acid and/or amino acid sequence of at least a portion of the envelope coding region of a virus from a biological sample obtained from a subject, where the portion of the envelope coding region comprises a portion of the coding region that can affect the activity of the envelope coding region on coreceptor tropism (210); (b) comparing the nucleic acid and/or amino acid sequence of the portion of the envelope coding region to sequence data stored in a database, the data comprising a plurality of sequences for the portion of the envelope coding region and for which the effect on coreceptor tropism has been evaluated, using a CBR analysis (220 and 230); and (c) determining the tropism of the virus from the biological sample (240).

Figure 3:
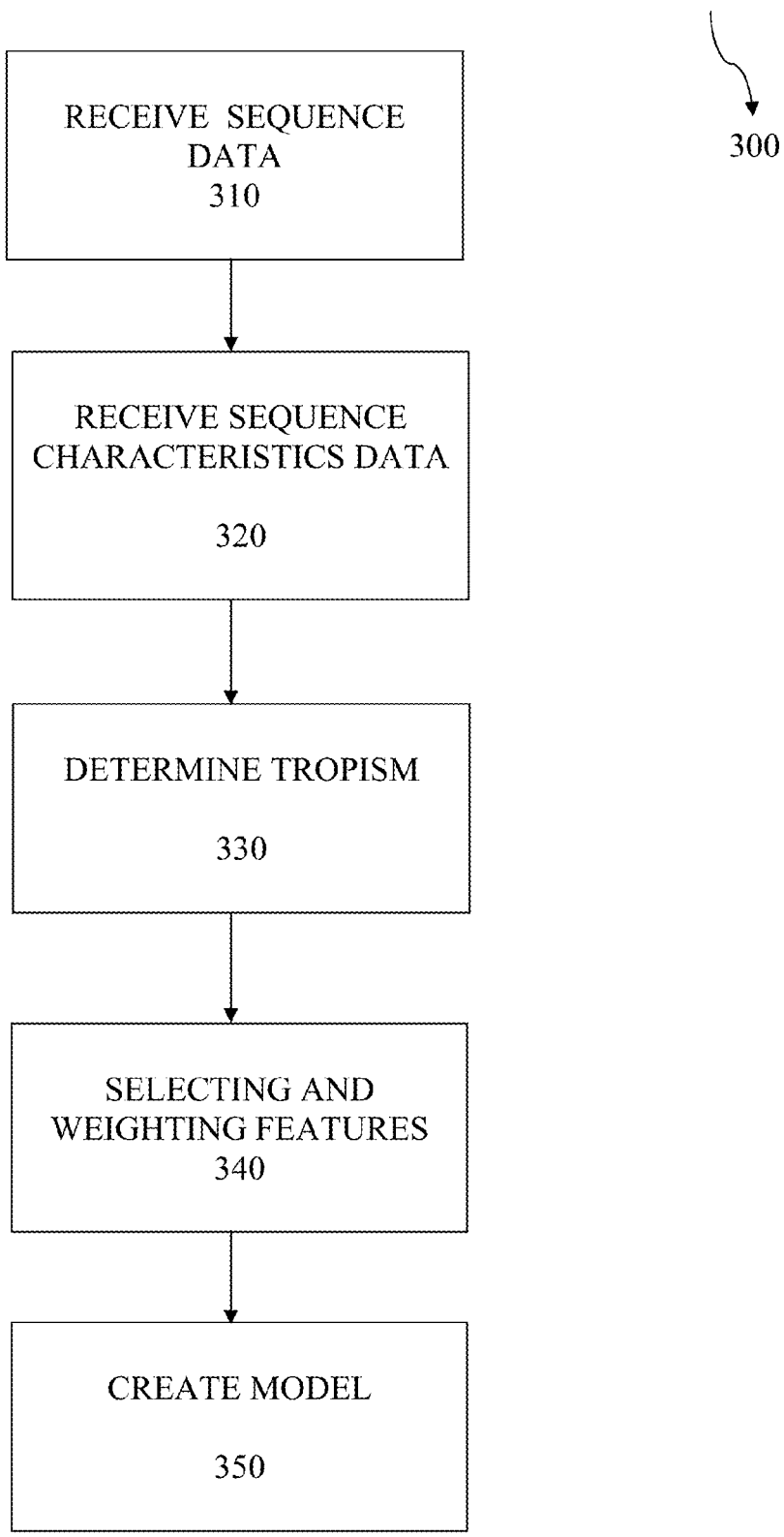
FIG. 3 shows a flow chart directed to a method of developing a model to predict coreceptor tropism according to certain embodiments.

FIG. 3 is a flow chart directed to a method 300 of developing a model to predict the effect of at least one coding region on drug susceptibility according to certain embodiments of the invention. The method shown in FIG. 3 will be described with respect to the systems 400 and 401 shown in FIGS. 4A and 4B and the electronic devices 500 and 501 shown in FIGS. 5A and 5B.

In the embodiment shown in FIG. 3, methods for predicting the coreceptor tropism of a virus are provided. For example, in some embodiments, the invention provides methods for predicting the effect of at least a portion of the envelope coding region on coreceptor tropism, the method comprising: (a) building a case library by obtaining an amino acid sequence, nucleic acid sequence, or both, of at least one portion of an envelope or envelope coding region from a plurality of viruses of different subtypes and different treatment history (310); (b) determining sequence characteristics of the amino acid sequence, nucleic acid sequence, or both of the at least one portion of the envelope or envelope coding region, wherein the sequence characteristics are nucleotide or amino acid mixtures, molecular weight, net charge, isoelectric point, molar composition, profile Hidden Markov Model (pHMM) values, or a combination thereof (320); (c) determining the tropism of the plurality of viruses (330); (d) selecting features and sequence characteristics that correlate with tropism determination for performing the similarity assessment (340); (e) assigning weights to each selected feature and sequence characteristic based on the significance of the correlation with tropism determination (340); and (f) generating a process for making a tropism call based on the selected features and sequence characteristics (350).

The methods of the invention may be applied to various coding regions or portions of coding regions. In certain embodiments, the at least one coding region comprises the envelope of a HIV virus. The disclosed methods may be used to determine if certain drugs cause sequence variations in a coding region that can affect the coreceptor tropism of the virus. For example, in certain embodiments, the subject has been exposed to a drug or other compound (e.g., an antibody) that blocks entry of the virus into a host cell.

The coding region sequences and tropism measurements as assessed for HIV from a particular subject may be compared to a database of tropism measurements and/or nucleic acid sequence data and/or amino acid sequence data. In certain embodiments, the database includes nucleic acid and/or amino acid sequences and corresponding tropism measurements for the envelope coding region from subjects who have been exposed to a drug that blocks entry of the virus into a host cell.

The Virus and Viral Samples

As noted herein, a mutation can be present in any type of virus, for example, any virus found in animals. In some embodiment of the invention, the virus includes viruses known to infect mammals, including dogs, cats, horses, sheep, cows, etc. In some embodiments, the virus is known to infect primates. In some such embodiments, the virus is known to infect humans. Examples of human viruses include, but are not limited to, human immunodeficiency virus ("HIV"), herpes simplex virus, cytomegalovirus virus, varicella zoster virus, other human herpes viruses, influenza A virus, respiratory syncytial virus, hepatitis A, B, and C viruses, rhinovirus, and human papilloma virus. In some embodiments of the invention, the virus is HIV. Preferably, the virus is human immunodeficiency virus type 1 ("HIV-1"). The foregoing are representative of certain viruses for which there is presently available anti-viral chemotherapy and represent the viral families retroviridae, herpesviridae, orthomyxoviridae, paramxyxovirus, picornavirus, flavivirus, pneumovirus, and hepadnaviridae. This invention can be used with other viral infections due to other viruses within these families, as well as viral infections arising from viruses in other viral families for which there is or there is not a currently available therapy.

A sequence associated with a change in coreceptor tropism according to the present invention can be found in a viral sample obtained by any means known in the art for obtaining viral samples. Such methods include, but are not limited to, obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus, and samples of other bodily fluids. In one embodiment, the sample is a blood, serum, or plasma sample.

In other embodiments, a mutation associated with a change in coreceptor tropism according to the present invention is present in a virus that can be obtained from a culture. In some embodiments, the culture can be obtained from a laboratory. In other embodiments, the culture can be obtained from a collection, for example, the American Type Culture Collection.

In some embodiments, a sequence associated with a change in coreceptor tropism according to the present invention is present in a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes or coding regions of interest can be incorporated into a vector. See, e.g., U.S. Pat. Nos. 5,837,464 and 6,242,187, and PCT publication WO 99/67427, each of which is incorporated herein by reference. In one embodiment, the coding regions are those that encode for an envelope protein.

In another embodiment, the intact virus need not be used. Instead, a part of the virus incorporated into a vector can be used. Preferably that part of the virus is used that is targeted by an anti-viral drug.

In another embodiment, a sequence associated with a change in coreceptor tropism is present in a genetically modified virus. The virus can be genetically modified using any method known in the art for genetically modifying a virus. For example, the virus can be grown for a desired number of generations in a laboratory culture. In one embodiment, no selective pressure is applied (e.g., the virus is not subjected to a treatment that favors the replication of viruses with certain characteristics), and new mutations accumulate through random genetic drift. In another embodiment, a selective pressure is applied to the virus as it is grown in culture (e.g., the virus is grown under conditions that favor the replication of viruses having one or more characteristics). In one embodiment, the selective pressure is an anti-viral treatment. Any known anti-viral treatment can be used as the selective pressure. In one embodiment, the virus is HIV and the selective pressure is a viral entry inhibitor. Any entry inhibitor can be used to apply the selective pressure. Examples of entry inhibitors include, but are not limited to, CD4 inhibitors, CCR5 inhibitors, CXCR4 inhibitors, binding site entry inhibitors, and blocking entry inhibitors. In some embodiments, the entry inhibitors may be selected from PRO 542, TNX-355, mAb B12, and mAb B4. In certain embodiments, the entry inhibitor is selected from the group consisting of BMS-488-403, PRO 542, mAb B4, mAb B12, TNX-355, UK-427857 (maraviroc), SCH-D (vicriviroc), GW-873140 (aplaviroc), AMD-11070, TAK-220, TAK-652 (TB-652, cenicriviroc, Tobira), Pro-140, and mAb004. In other embodiments, the entry inhibitor is selected from the group consisting of TNX-355, UK-427857 (maraviroc), SCH-D (vicriviroc), GW-873140 (aplaviroc), AMD-11070, TAK-652 (TB-652, cenicriviroc), and TAK-220. In certain embodiments, the entry inhibitor is selected from the group consisting of UK-427857 (maraviroc), SCH-D (vicriviroc), GW-873140 (aplaviroc), TAK-652 (TB-652, cenicriviroc), TAK-220, INCB9471, CCR % monoclonal antibodies (e.g., PRO-140 and HGSI-004). In certain embodiments, the entry inhibitor is selected form the group consisting of AMD-3100, AMD-11070, KRH-3140, and KRH-3955. By treating HIV cultured in vitro with an entry inhibitor, one can select for mutant strains of HIV that have an increased resistance to the entry inhibitor. The stringency of the selective pressure can be manipulated to increase or decrease the survival of viruses not having the selected-for characteristic.

In another aspect, a sequence associated with a change in coreceptor tropism or drug susceptibility according to the present invention is made by mutagenizing a virus, a viral genome, or a part of a viral genome. Any method of mutagenesis known in the art can be used for this purpose. In one embodiment, the mutagenesis is essentially random. In another embodiment, the essentially random mutagenesis is performed by exposing the virus, viral genome, or part of the viral genome to a mutagenic treatment. In another embodiment, a gene that encodes a viral protein that is the target of an anti-viral therapy is mutagenized. Examples of essentially random mutagenic treatments include, for example, exposure to mutagenic substances (e.g., ethidium bromide, ethylmethanesulphonate, ethyl nitroso urea (ENU)) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., Proc. Nat. Acad. Sci., 76:5918-5922 (1979); Russell, Environmental Mutagens and Carcinogens: Proceedings of the Third International Conference on Environmental Mutagens (1982). One of skill in the art will appreciate that while each of these methods of mutagenesis is essentially random, at a molecular level, each has its own preferred targets.

In another aspect, a mutation that might affect coreceptor tropism or the sensitivity of a virus to an anti-viral therapy is made using site-directed mutagenesis. Any method of site-directed mutagenesis known in the art can be used. See, e.g., Sambrook et al., Molecular Cloning: A Laboratory Manual, Cold Spring Harbor Laboratory, (3rd ed., 2001); and Ausubel et al., Current Protocols in Molecular Biology (1989). The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In some embodiments, a gene or a portion of a gene is subjected to site-directed mutagenesis because it encodes a protein that is known or suspected to be a target of an anti-viral therapy, e.g., the gene encoding the HIV protease. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains having decreased susceptibility to the anti-viral treatment. In another embodiment, the mutagenized nucleotides encode amino acid residues that are adjacent to or near in the primary sequence of the protein residues known or suspected to interact with an anti-viral compound or known or suspected to be mutated in viral strains having decreased susceptibility to an anti-viral treatment. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having decreased susceptibility to an anti-viral treatment. In another embodiment, the mutagenized nucleotides encode amino acid residues in or near the active site of a protein that is known or suspected to bind to an anti-viral compound. See, e.g., Sarkar and Sommer, Biotechniques, 8:404-407 (1990).

Detecting the Sequence of an Envelope Coding Region

The presence or absence of a mutation associated with a change in coreceptor tropism or drug susceptibility according to the present invention in a virus can be detected by any means known in the art for detecting a mutation. The mutation can be detected in the viral gene that encodes a particular protein, or in the protein itself, e.g., in the amino acid sequence of the protein.

In some embodiments, the mutation is in the viral genome. Such a mutation can be in, for example, a gene encoding a viral protein, in a cis or trans acting regulatory sequence of a gene encoding a viral protein, an intergenic sequence, or an intron sequence. The mutation can affect any aspect of the structure, function, replication, or environment of the virus that changes its susceptibility to an anti-viral treatment. In one embodiment, the mutation is in a gene encoding a viral protein that is the target of an anti-viral treatment.

A mutation within a viral coding region can be detected by utilizing a number of techniques. Viral DNA or RNA can be used as the starting point for such assay techniques, and may be isolated according to standard procedures which are known to those of skill in the art.

The detection of a mutation in specific nucleic acid sequences, such as in a particular region of a viral gene, can be accomplished by a variety of methods including, but not limited to, restriction-fragment-length-polymorphism detection based on allele-specific restriction-endonuclease cleavage, mismatch-repair detection, binding of MutS protein, denaturing-gradient gel electrophoresis, single-strand-conformation-polymorphism detection, RNAase cleavage at mismatched base-pairs, chemical or enzymatic cleavage of heteroduplex DNA, methods based on oligonucleotide-specific primer extension, genetic bit analysis, oligonucleotide-ligation assay, oligonucleotide-specific ligation chain reaction ("LCR"), gap-LCR, radioactive or fluorescent DNA sequencing using standard procedures well known in the art, and peptide nucleic acid (PNA) assays.

In addition, viral DNA or RNA may be used in hybridization or amplification assays to detect abnormalities involving gene structure (e.g., insertions, deletions, point mutations, and genomic rearrangements. Such assays include, but are not limited to, Southern analyses, single stranded conformational polymorphism analyses (SSCP), and PCR analyses.

Such diagnostic methods for the detection of a gene-specific mutation can involve for example, contacting and incubating the viral nucleic acids with one or more labeled nucleic acid reagents including recombinant DNA molecules, cloned genes, or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

Alternative diagnostic methods for the detection of gene specific nucleic acid molecules may involve their amplification, e.g., by PCR, followed by the detection of the amplified molecules using techniques well known to those of skill in the art. The resulting amplified sequences can be compared to those which would be expected if the nucleic acid being amplified contained only normal copies of the respective gene in order to determine whether a gene mutation exists.

Additionally, the nucleic acid can be sequenced by any sequencing method known in the art. For example, the viral DNA can be sequenced by the dideoxy method of Sanger et al., Proc. Natl. Acad. Sci., 74:5463 (1977), as further described by Messing et al., Nuc. Acids Res., 9:309 (1981), or by the method of Maxam et al., Methods in Enzymol., 65:499 (1980). See also techniques described in Sambrook et al., Molecular Cloning: A Laboratory Manual, Cold Spring Harbor Lab. (3d ed., 2001); and Ausubel et al., Current Protocols in Molecular Biol. (1989).

Antibodies directed against the viral gene products, e.g., viral proteins or viral peptide fragments, can also be used to detect mutations in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

Measuring Phenotypic Viral Tropism or Susceptibility of a Virus to an Entry Inhibitor Any method known in the art can be used to determine the phenotypic viral tropism or susceptibility of a mutant virus or population of viruses to entry inhibitor anti-viral therapy. See e.g., U.S. Pat. Nos. 5,837,464, 6,242,187, and 8,114,585, the entire contents of which are incorporated herein by reference.

In some embodiments a phenotypic analysis is performed, e.g., the susceptibility of the virus to a given anti-viral agent is assayed with respect to the susceptibility of a reference virus without the mutations. This is a direct, quantitative measure of tropism or drug susceptibility and can be performed by any method known in the art to determine the tropism or susceptibility of a virus to an entry inhibitor. In some embodiments, the phenotypic analysis is performed using an enhanced sensitivity TROFILE assay (ESTA, Monogram Biosciences, South San Francisco, Calif.). The TROFILE assay is a single-cycle recombinant virus assay in which a pseudovirus is generated from full length envelope (env) coding regions derived from a patient's virus population. The complete envelope is used to determine viral tropism taking into account determinants that lie outside the V3 loop.

An example of drug susceptibility methods includes, but is not limited to, determining the fold change in $IC_{50}$ values with respect to a reference virus or determining the maximum inhibition percentage as compared to that of a reference virus. Phenotypic susceptibility testing measures the ability of a specific viral strain to grow in vitro in the presence of a drug inhibitor. A virus is less susceptible to a particular drug when more of the drug is required to inhibit viral activity, versus the amount of drug required to inhibit the reference virus, or when the drug can never fully inhibit viral activity no matter how much drug is used.

In another embodiment, the phenotypic analysis is performed using recombinant virus assays ("RVAs"). RVAs use virus stocks generated by homologous recombination between viral vectors and viral gene sequences, amplified from the subject virus. In some embodiments, the viral vector is a HIV vector and the viral gene sequences are protease and/or reverse transcriptase sequences.

In some embodiments, the phenotypic analysis is performed using a PHENOSENSE assay (Monogram Biosciences, South San Francisco, Calif.). See Petropoulos et al., Antimicrob. Agents Chemother. Vol. 44, pp. 920-928 (2000); U.S. Pat. Nos. 5,837,464 and 6,242,187. PHENOSENSE is a phenotypic assay that achieves the benefits of phenotypic testing and overcomes the drawbacks of previous assays. Because the assay has been automated, PHENOSENSE offers higher throughput under controlled conditions. The result is an assay that accurately defines the susceptibility profile of a subject's HIV isolates to all currently available antiretroviral drugs, and delivers results directly to the physician within about 10 to about 15 days of sample receipt. PHENOSENSE is accurate and can obtain results with only one round of viral replication, thereby avoiding selection of subpopulations of virus. The results are quantitative, measuring varying degrees of drug susceptibility, and sensitive—the test can be performed on blood specimens with a viral load of about 500 copies/mL and can detect minority populations of some drug-resistant virus at concentrations of 10% or less of total viral population. Furthermore, the results are reproducible and can vary by less than about 1.4-2.5 fold, depending on the drug, in about 95% of the assays performed.

PHENOSENSE can be used with nucleic acids from amplified viral gene sequences. As discussed herein, the sample containing the virus may be a sample from a human or an animal infected with the virus or a sample from a culture of viral cells. In one embodiment, the viral sample comprises a genetically modified laboratory strain.

A resistance test vector ("RTV") can then be constructed by incorporating the amplified viral gene sequences into a replication defective viral vector by using any method known in the art of incorporating gene sequences into a vector. In one embodiment, restrictions enzymes and conventional cloning methods are used. See Sambrook et al., MOLECULAR CLONING: A LABORATORY MANUAL, COLD SPRING HARBOR LABORATORY, (3.sup.rd ed., 2001); and Ausubel et al., CURRENT PROTOCOLS IN MOLECULAR BIOLOGY (1989). In a some embodiments, ApaI and PinAI restriction enzymes are used. Preferably, the replication defective viral vector is the indicator gene viral vector ("IGVV"). In some embodiments, the viral vector contains a means for detecting replication of the RTV. Preferably, the viral vector contains a luciferase expression cassette.

The assay can be performed by first co-transfecting host cells with RTV DNA and a plasmid that expresses the envelope proteins of another retrovirus, for example, amphotropic murine leukemia virus (MLV). Following transfection, virus particles can be harvested and used to infect fresh target cells. The completion of a single round of viral replication can be detected by the means for detecting replication contained in the vector. In some embodiments, the completion of a single round of viral replication results in the production of luciferase. Serial concentrations of anti-viral agents can be added at either the transfection step or the infection step.

Susceptibility to the anti-viral agent can be measured by comparing the replication of the vector in the presence and absence of the anti-viral agent. For example, susceptibility to the anti-viral agent can be measured by comparing the luciferase activity in the presence and absence of the anti-viral agent. Susceptible viruses would produce low levels of luciferase activity in the presence of antiviral agents, whereas viruses with reduced susceptibility would produce higher levels of luciferase activity.

In some embodiments, PHENOSENSE is used in evaluating the phenotypic susceptibility of HIV-1 to anti-viral drugs. Preferably, the anti-viral drug is an entry inhibitor. In some embodiments, the reference viral strain is HIV strain NL4-3 or HXB-2. Other assays for evaluating the phenotypic susceptibility of a virus to anti-viral drugs known to one of skill in the art can be used. See, e.g., Shi and Mellors, 1997, Antimicrob. Agents Chemother. 41:2781-85; Gervaix et al., 1997, Proc. Natl. Acad. Sci. 94:4653-58; Race et al., 1999, AIDS 13:2061-2068, and U.S. Pat. Nos. 5,436,131 and 6,103,462, the entire contents of which are incorporated herein by reference.

Illustrative System

FIGS. 4A and 4B show embodiments of illustrative systems suitable for executing one or more of the methods disclosed herein. For example, FIGS. 4A and 4B show diagrams depicting illustrative computing devices in illustrative computing environments according to some embodiments. The system 400 shown in FIG. 4A includes a computing device 410, a network 420, and a data store 430. The computing device 410 and the data store 430 are connected to the network 420. In this embodiment, the computing device 410 can communicate with the data store 430 through the network 420.

The systems 400 shown in FIGS. 4A and 4B include a computing device 410. A suitable computing device for use with some embodiments may comprise any device capable of communicating with a network, such as network 420, or capable of sending or receiving information to or from another device, such as data store 430. A computing device can include an appropriate device operable to send and receive requests, messages, or information over an appropriate network. Examples of such suitable computing devices include personal computers, cell phones, handheld messaging devices, laptop computers, tablet computers, set-top boxes, personal data assistants (PDAs), servers, or any other suitable computing device. In some embodiments, the computing device 410 may be in communication with other computing devices directly or through network 420, or both. For example, in the system 401 of FIG. 4B, the computing device 410 is in direct communication with data store 430, such as via a point-to-point connection (e.g. a USB connection), an internal data bus (e.g. an internal Serial ATA connection) or external data bus (e.g. an external Serial ATA connection). In one embodiment, computer device 410 may comprise the data store 430. For example, in one embodiment, the data store 430 may comprise a hard drive that is a part of the computer device 410.

A computing device typically will include an operating system that provides executable program instructions for the general administration and operation of that computing device, and typically will include a tangible computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

In the embodiment shown in FIG. 4A, the network 420 facilitates communications between the computing device 410 and the data store 430. The network 420 may be any suitable number or type of networks or links including, but not limited to, a dial-in network, a local area network (LAN), wide area network (WAN), public switched telephone network (PSTN), the Internet, an intranet, or any combination of hard-wired and/or wireless communication links. In one embodiment, the network 420 may be a single network. In other embodiments, the network 420 may comprise two or more networks. For example, the computing device 410 may be connected to a first network and the data store 430 may be connected to a second network and the first and the second network may be connected. In one embodiment, the network 420 may comprise the Internet. Components used for such a system can depend at least in part upon the type of network and/or environment selected. Protocols and components for communicating via such a network are well known and will not be discussed herein in detail. Communication over the network can be enabled by wired or wireless connections, and combinations thereof. Numerous other network configurations would be obvious to a person of ordinary skill in the art.

The systems 400 shown in FIGS. 4A and 4B include a data store 430. The data store 430 can include several separate data tables, databases, or other data storage mechanisms and media for storing data relating to a particular aspect. It should be understood that there can be many other aspects that may need to be stored in the data store, such as to access right information, which can be stored in any appropriate mechanism or mechanisms in the data store 430. The data store 430 may be operable to receive instructions from the computing device 410 and obtain, update, or otherwise process data in response thereto.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

Illustrative Computing Device

FIGS. 5A and 5B show block diagrams depicting exemplary computing devices according to various embodiments. According to the embodiment shown in FIG. 5A, the computing device 500 comprises a computer-readable medium such as memory 510 coupled to a processor 520 that is configured to execute computer-executable program instructions (or program code) and/or to access information stored in memory 510. A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, CAM, DDR, flash memory such as NAND flash or NOR flash, an ASIC, a configured processor, optical storage, magnetic tape or other magnetic storage, or any other medium from which a computer processor can read instructions. In one embodiment, the computing device 500 may comprise a single type of computer-readable medium such as random access memory (RAM). In other embodiments, the computing device 500 may comprise two or more types of computer-readable medium such as random access memory (RAM), a disk drive, and cache. The computing device 500 may be in communication with one or more external computer-readable mediums such as an external hard disk drive or an external DVD drive.

Embodiments of the systems for carrying out the methods for predicting tropism can be implemented in digital electronic circuitry, in computer hardware, firmware, software, or a combination thereof. As discussed above, the embodiment shown in FIG. 5A comprises a processor 520 which is configured to execute computer-executable program instructions and/or to access information stored in memory 510. Such processors may comprise, or may be in communication with, media, for example tangible computer-readable media that may store instructions that when executed by the processor, can cause the processor to perform the steps described herein as carried out, or assisted, by a processor. The instructions may comprise processor-specific instructions generated by a compiler and/or an interpreter from code written in any suitable computer-programming language including, for example, C, C++, C#, Visual Basic, Java, Python, Perl, JavaScript, and ActionScript®. In an embodiment, the computing device 500 comprises a single processor 520. In other embodiments, the device 500 comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device 500 as shown in FIG. 5A comprises a network interface 530. In some embodiments, the network interface 530 is configured for communicating via wired or wireless communication links. For example, the network interface 530 may allow for communication over networks via Ethernet, IEEE 802.11 (Wi-Fi), 802.16 (Wi-Max), Bluetooth, infrared, etc. As another example, network interface 530 may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, such as the embodiment 501 shown in FIG. 5B, the computing device may include a data store 560 in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device 500 shown in FIG. 5A is in communication with various user interface devices 540 and a display 550. Display 550 may use any suitable technology including, but not limited to, LCD, LED, CRT, and the like.

In various embodiments, suitable computing devices may be a server, a desktop computer, a personal computing device, a mobile device, a tablet, a mobile phone, or any other type of electronic devices appropriate for providing one or more of the features described herein. In at least one aspect, the invention provides systems for carrying out the analysis described above. Thus, in some embodiments, the present invention comprises a computer-readable medium on which is encoded programming code for the prediction methods described herein. Also in some embodiments, such as described above with respect to FIGS. 4 and 5, the invention comprises a system comprising a processor in communication with a computer-readable medium, the processor configured to perform the generalized ridge regression methods described herein. Suitable processors and computer-readable media for various embodiments of the present invention are described in greater detail above.

Thus, in certain embodiments, the invention comprises a system for predicting coreceptor tropism of a virus comprising: a computer readable medium; and a processor in communication with the computer readable medium, the processor configured to apply a case based reasoning (CBR) analysis to estimate the effect of at least a portion of an envelope or envelope coding region. The processor may, in certain embodiments, be further in communication with a database comprising data for a plurality of sequences for the portion of the envelope coding region, where the processor is configured to compare the nucleic acid and/or amino acid sequence of the portion of the envelope coding region to the data of the plurality of sequences for the portion of the envelope or envelope coding region to determine if there is a particular feature in the sequence obtained from the biological sample obtained from the subject.

In other embodiments, the invention comprises a computer readable medium on which is encoded program code for predicting the effect of the portion of the envelope or envelope coding region on tropism, the program code comprising code for applying a CBR analysis to estimate the effects of the sequence of the portion of the envelope or envelope coding region on tropism. In certain embodiments, the programming code comprises code configured to compare the amino acid and/or nucleic acid sequence of the portion of the envelope or envelope coding region to the data for a plurality of sequences for the portion of the envelope or envelope coding region stored in a database to determine if there is a particular feature present in the portion of the envelope or envelope coding region in the virus from the biological sample obtained from the subject.

For some embodiments of the systems and computer readable media of the invention, the subject may be exposed to a drug or other compound (e.g., an antibody) that affects viral entry.

Some embodiments of the systems and computer readable media of the invention may be applied to various portions of the envelope or envelope coding region. In certain embodiments, the portion of the envelope coding region comprises the V3 loop or coding region of an HIV virus.

As noted herein, the sequence of the portion of the envelope coding region for a particular subject may be compared to a database of amino acid and/or nucleic acid sequences and tropism as assessed for a plurality of subjects. Thus, in certain embodiments of the systems and computer readable media, the database comprises data for tropism as measured in a plurality of samples from which the sequence of the portion of the envelope or envelope coding region was determined. Also, the database may include amino acid and/or nucleic acid sequence for the envelope or envelope coding region from a plurality of subjects who have been exposed to a drug that can affect viral entry.

A variety of statistical techniques may be employed in the present assays, methods, and systems. In one embodiment, the starting point may comprise data generated from a database of assays for tropism and gene sequences. Once the data has been collected, it may be compiled and/or transformed if necessary using any standard spreadsheet software such as Microsoft Excel, FoxPro, Lotus, or the like. In one embodiment, the data are entered into the system for each experiment. Alternatively, data from previous runs are stored in the computer memory and used as required.

At each point in the analysis, the user may input instructions via a keyboard, floppy disk, remote access (e.g., via the internet), or other access means. The user may enter instructions including options for the run, how reports should be printed out, and the like. Also, at each step in the analysis, the data may be stored in the computer using a storage device common in the art such as disks, drives or memory. As is understood in the art, the processor and I/O controller are required for multiple aspects of computer function. Also, in a embodiment, there may be more than one processor.

The data also may be processed to remove noise. In some cases, the user, via the keyboard, floppy disk, or remote access, may want to input variables or constraints for the analysis, as for example, the threshold for determining noise.

EXAMPLES

The present invention may be better understood by reference to the following non-limiting examples. While the invention has been described and illustrated with reference to certain embodiments thereof, those skilled in the art will appreciate that various changes, modifications, and substitutions can be made therein without departing from the spirit and scope of the invention. All patents, published patent applications, and other non-patent references referred to herein are incorporated by reference in their entireties.

Example 1

Data Collection and Construction of the Case Library

A case-based reasoning (CBR) system was constructed to perform tropism prediction based on the V3 loop region of the envelope of the HIV-1 sequence. The CBR algorithm consisted of a case library of 732 V3 sequences with a matched phenotype as determined by enhanced sensitivity TROFILE assay (ESTA, Monogram Biosciences, South San Francisco, Calif.). Sequence characteristics that provide additional information about the coreceptor usage were extracted, including: 1) count of nucleotide and amino acid mixtures in the V3 loop; 2) peptide statistics; 3) score generated from the profile Hidden Markov Model (pHMM) developed based on a set of treatment-naïve and R5 tropic samples.

Viral sequences were obtained from Monogram Biosciences' commercial patient testing database as well as TORO (Reynes et al., 2007, AIDS Patient Care STDS 21(8):533-43) and LTM cohorts (Goetz et al., 2009, J. Acquire. Immune Defic. Syndr. 50:259-66). V3 loop sequences were derived using population sequencing. In the case of amino acid mixtures, the ambiguity was resolved in favor of the amino acid more prevalent in the X4 tropic set using a PSSM-based approach as previously described (Jensen et al., 2003, J. Virol. 77(24):13376-88). Amino acid insertions and deletions were coded as an insertion and a gap character, respectively. All final sequences were 35 amino acids in length with no ambiguous residues. Duplicate sequences were removed from this set. Phenotypic coreceptor tropism was determined by the Monogram Biosciences' Enhanced Sensitivity TROFILE Assay (ESTA, Monogram Biosciences, South San Francisco, Calif.) (Goetz et al., 2009, J. Acquir. Immune Defic. Syndr. 50(3):259-66). In all, 732 unique V3 sequences were identified from as many patients, resulting in 406 R5 tropic viruses and 326 Dual/Mixed (DM) or X4 tropic viruses. These sequences were used to construct a case library.

Example 2

Evaluation of Sequence Characteristics of the Case Library

Figure 6:
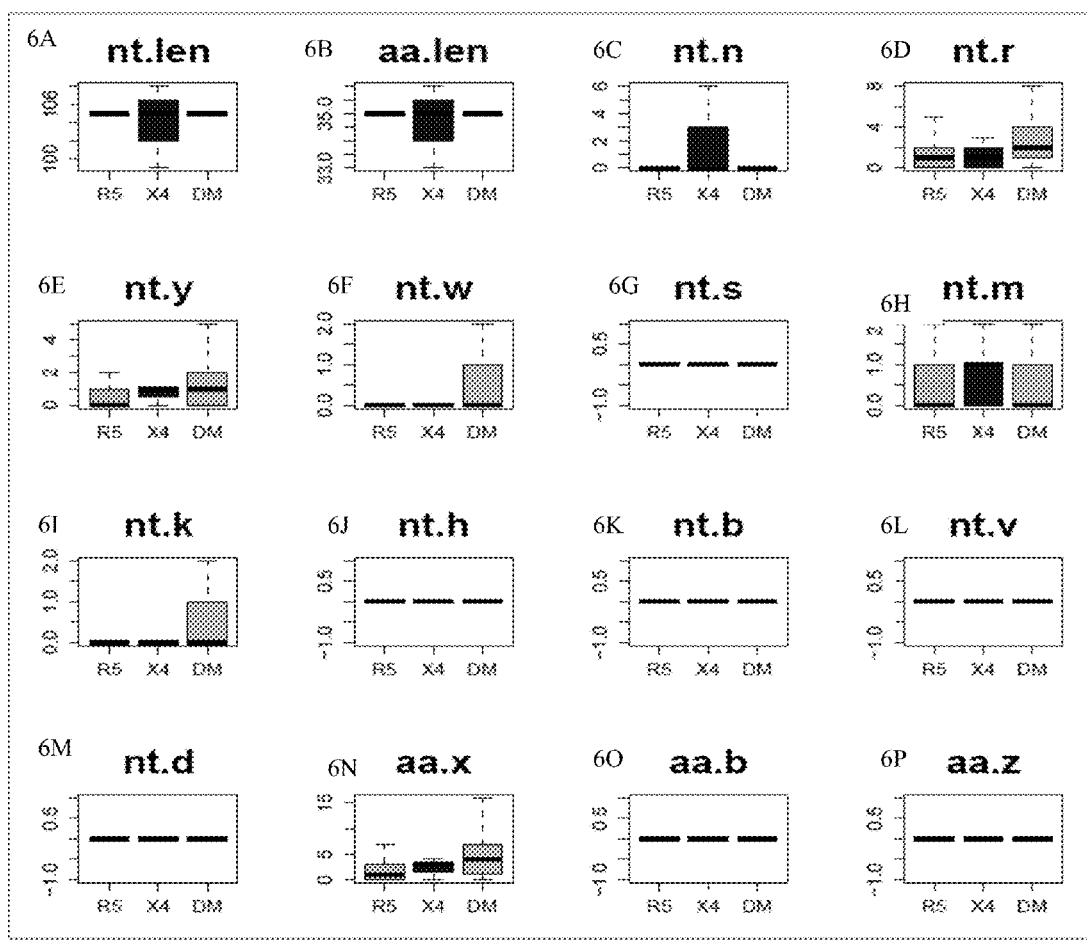

First, the correlation between sequence length, amino acid and nucleotide mixtures, and tropism were evaluated using univariate analysis. In order to identify significant associations between a given attribute and coreceptor usage as determined by ESTA, Fisher's Exact Test (FET) was performed, and an odds ratio was calculated based on presence or absence of a feature in the X4-using set. Mutations and attributes with statistically significant correlation ($p<0.05$ after Bonferroni correction) were included as the data fields of the case library. The log of the odds ratio was used to assign a weight to every position in the amino acid sequence as well as all selected features. As displayed in FIG. 6, significant association was found between DM tropism and presence of the nucleotide ambiguities R (G or A), Y (T or C), W (A or T) and K (T or G). There was also a correlation of mixed amino acids and DM tropism, but not with the specific ambiguities of B (Asp or Asn) or Z (Glu or Gln).

Example 3

Evaluation of Physiochemical Characteristics of the Case Library

Figure 7:
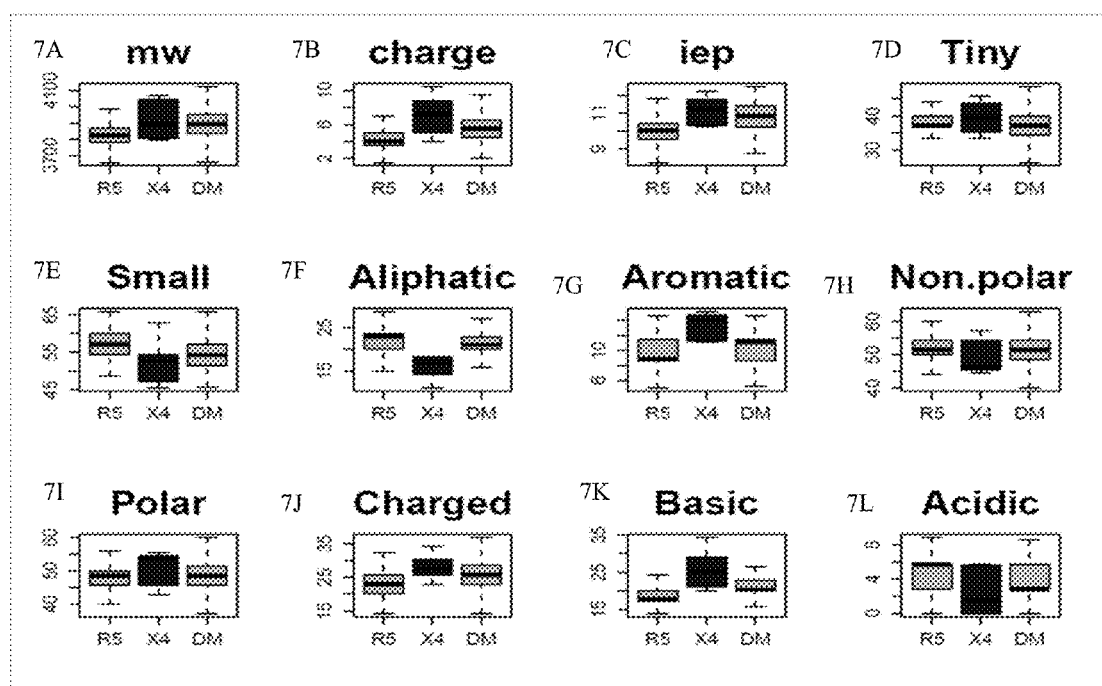
FIGS. 7A through 7L are graphs showing the distribution of physiochemical characteristics of the viruses grouped by tropism as determined by ESTA. MW refers to molecular weight (FIG. 7A, measured in Daltons of combined V3 amino acids), charge refers to net charge (FIG. 7B, measured as overall net charge of combined V3 amino acids), and iep refers to isoelectric point (FIG. 7C, measured as overall isoelectric point of combined V3 amino acids). Tiny refers to amino acid residues with very small side chains, including alanine, cysteine, glycine, serine, or threonine (FIG. 7D). Small refers to amino acids with small side chains, including alanine, aspartic acid and asparagine, cysteine, aspartic acid, glycine, asparagine, proline, serine, threonine, or valine (FIG. 7E). Aliphatic refers to alanine, isoleucine, leucine, or valine residues (FIG. 7F). Aromatic refers to phenylalanine, histidine, tryptophan, or tyrosine residues (FIG. 7G). Non-polar refers to alanine, cysteine, phenylalanine, glycine, isoleucine, leucine, methionine, proline, valine, tryptophan, or tyrosine residues (FIG. 7H). Polar refers to aspartic acid, glutamic acid, histidine, lysine, asaparagine, glutamine, arginine, serine, threonine, or glutamic acid and glutamine residues (FIG. 7I). Charged refers to aspartic acid and asparagine, aspartic acid, glutamic acid, histidine, lysine, arginine, or glutamic acid and glutamine residues (FIG. 7J). Basic refers to histidine, lysine, or arginine residues (FIG. 7K), and Acidic refers to aspartic acid or asparagines, aspartic acid, glutamic acid, or glutamic acid and glutamine residues (FIG. 7L). The x axis in FIGS. 7A-7L shows viruses that were R5, X4, or dual/mixed tropic. The y axis in FIGS. 7C-7L represents the distribution of the particular property noted above (and on the figure) within the training set's sequences.

Subsequently, additional sequence characteristics were examined, such as the count of nucleotide and amino acid mixtures in the original sequence, peptide statistics, and profile Hidden Markov Model (pHMM) values. Statistical analysis was performed to evaluate the importance of these attributes relative to tropism determination. The PEPSTATS program (The Next Generation Biology Workbench) was used to analyze each sequence in the case library and determined its physiochemical profile. Among the characteristics calculated were molecular weight, net charge (charge), and isoelectric point (iep). Additionally the molar composition by biochemical class (aliphatic, aromatic, polar, charged, basic, acidic, tiny, and small) of the V3 peptide was evaluated. The distribution of each characteristic across the three tropism groups is shown in FIGS. 7A-7P. Several of these attributes show significant distinction between R5 and X4/DM tropisms. The graphs for net charge and iep show similar profiles, as does the charged amino acid group. This is expected since the isoelectric point is driven by the net charge, which is in turn driven by the percentage of charged residues that comprise a peptide. Inferences about the nature of the charged residues are made from comparing the basic and acidic composition graphs, with the graph for basic residues resembling the pattern for charged, charge, and iep. These data suggest a preference for X4/DM tropic viruses to have V3 sequences that are more basic in nature and to have a more basic local isoelectric point.

Given that the coreceptors CCR5 and CXCR4 are different proteins with different physiochemical characteristics in the local environment of their V3 binding sites, it was decided to explore whether there were significant physiochemical shifts in the nature of the V3 peptide that correlated with coreceptor usage. Physiochemical properties of the V3 amino acid peptides were determined using the accepted conventions introduced by the PEPSTAT program (Whitcomb et al., 2007, Antimicrob. Agents Chemother. 51(2): 566-75).

Figure 8:
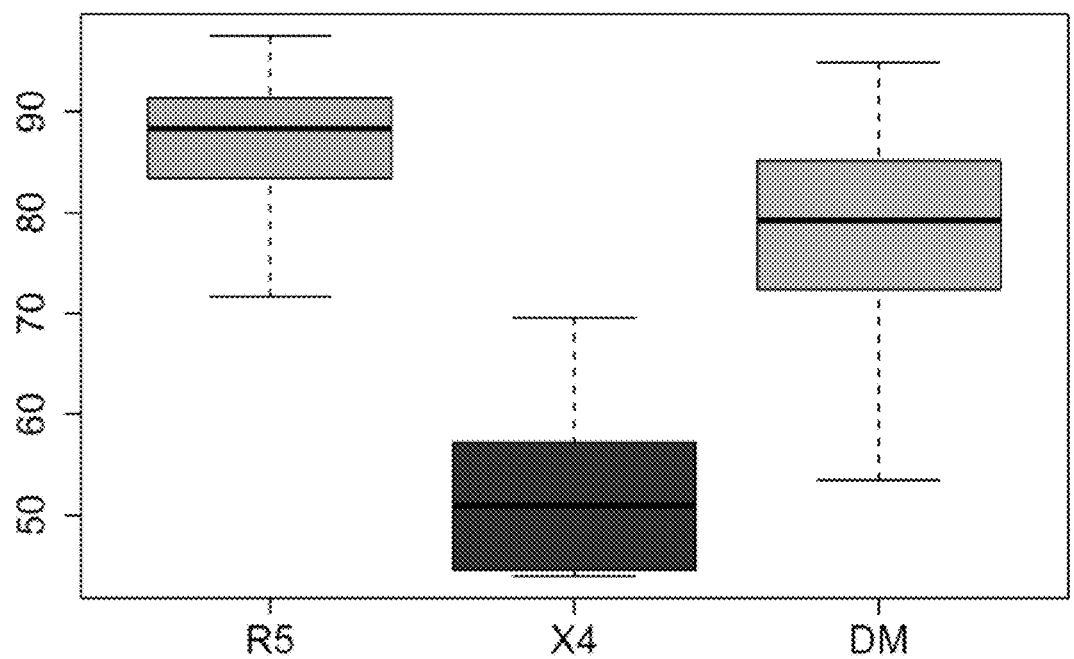
FIG. 8 is a graph showing the distribution of R5 HMM score in the case library grouped by tropism. The x axis shows viruses that were R5, X4, or dual/mixed tropic. The y axis shows the R5 HMM score.

In an attempt to capture the "R5-ness" of the virus, a score generated based on a pHMM that was developed using a subset of treatment naïve and R5-using samples was obtained and examined. Profile HMMs are statistical models of multiple sequence alignments, which capture position specific information regarding how conserved a residue may be in that alignment and which residues are most likely to occur. When a sequence is compared against the pHMM, a score is given that measures how well it fits the model. Since it was desired to capture the "R5-ness" of the virus, treatment naïve, R5-using samples were used to minimize the possible impurity of the virus population resulting from treatment exposure. Using this subset of samples, a multiple sequence alignment was created and was used to generate a pHMM by applying the HMMR 3.0 application suite (Rice et al., 2000, Trends Genet. 16(6):276-77; Eddy, 1995, Proc. Int. Conf. Intell. Syst. Mol. Biol. 3:114-20; Eddy, 1996, Curr. Opin. Struct. Biol. 6(3):361-65). This score is referred to here as the HMM Score. As shown in FIG. 8, pure X4 tropic viruses have distinctly lower HMM scores compared to the R5 and DM sets, while scores derived from DM viruses are generally lower than R5-using samples, but higher than the X4 set.

Figure 9:
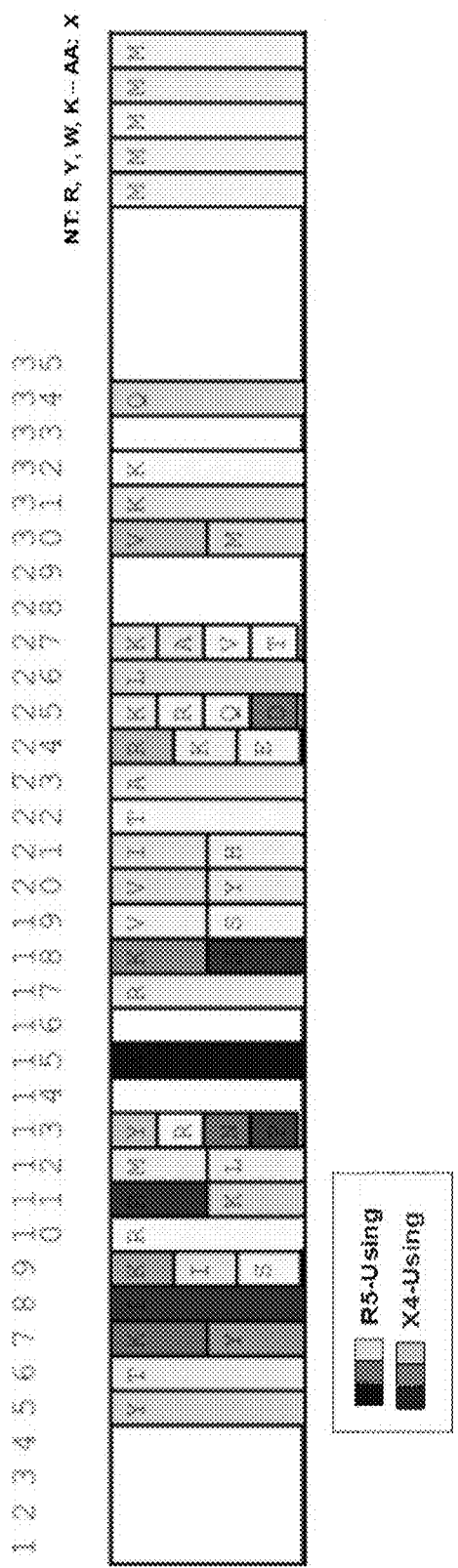
FIG. 9 is a schematic showing selected features and weights based on Fisher's Exact test results. The numbers above the boxes represent the position of the amino acid in the V3 loop of Env, and the letters within the boxes represent mutations from the sequence present its association with X4 or R5 usage. Red to light pink indicates high to low association of the amino acid with X4 usage, and blue to light-blue indicates high to low association of the amino acid with R5-usage. The last five boxes to the right represent the odds ratio of the increased occurrence of the 4 specific nucleotide mixtures (R, Y, W, and K), and the amino acid mixture X in X4-using viruses.

We then examined these additional attributes using univariate analysis to identify features significantly associated with coreceptor usage. Amino acid positions and substitutions as well as quantity and quality of sequence ambiguities, peptide statistics, and HMM score were evaluated using Fisher's Exact test. Graphical representation of the features significantly (corrected p-value<0.05) associated with coreceptor tropism and their weight as derived from the odds ratios is shown in FIG. 9. In all, the amino acid sequence of the V3 loop, the count of specific nucleotide and amino acid mixtures, selected peptide statistics, and the HMM score were the chosen elements of the case library.

Example 4

Similarity Metric and Adaptation of the Case Based Reasoning System

To evaluate a query sequence against the case library, the query was compared to each member of the case library. All amino acid positions were examined for a match between the query sequence and the case in the library. For attributes that describe the sequence characteristics as a continuous value, similarity was defined as a range for the absolute difference. Based on the odds ratios calculated in the FET analysis, an array of weights was generated for the 35 amino acid sites, as well as the additional features, in the case library. When performing the comparison between a new problem and the cases stored in the library, for each identical amino acid and for every similar feature, the respective weight was added to calculate a total similarity score.

An adaptation strategy was defined that maximizes the X4 sensitivity. Based on the similarity scores calculated for all cases in the library, if any of the top three scoring cases is DM or X4, then the query is predicted to be X4-using (X4 tropic), otherwise it is predicted to be R5-using (R5 tropic) (FIG. 9).

Example 5

Evaluation of the Case Based Reasoning System

The predictive power of the case based reasoning (CBR) system was evaluated by performing Leave-One-Out-Cross-Validation (LOOCV) in which each of the 732 cases was temporarily removed from the case library and was then presented to the CBR tool as a case for tropism prediction. Accuracy of the CBR system was evaluated as the ability to predict coreceptor tropism compared to ESTA (number of correctly predicted tropisms/number of all cases). True positive (TP) rate or sensitivity, true negative (TN) rate or specificity, number of false positive (FP) and false negative (FN) cases were obtained, and the overall concordance as compared to ESTA for detection of X4 usage within our datasets. These results are shown in Table 1.

The CBR algorithm achieved a specificity of 73.2%, a sensitivity of 89.6% and an overall accuracy of 80.5% in the training set. Furthermore, the training set of 732 V3 sequences was used to construct a PSSM and a SVM model. The 11/25 rule was also applied on this dataset. For comparison, the performance of these additional predictors is shown in Table 1. The sensitivity of the CBR algorithm was the highest among the bioinformatics predictors investigated. This improved sensitivity was expected as the adaptation strategy of the CBR tool was adjusted to maximize the sensitivity to detect X4 usage while maintaining an adequate accuracy.

TABLE 1

CBR performance in the training set, and comparison
with SVM, PSSM, and the 11/25 rule

|  | Prediction Method | TN | FP | FN | TP | Concordance | Spec. | Sens. |
|---|---|---|---|---|---|---|---|---|
| Training set N = 732 | CBR | 297 | 109 | 34 | 292 | 80.5% | 73.2% | 89.6% |
|  | SVM | 376 | 30 | 56 | 270 | 88.3% | 92.6% | 82.8% |
|  | PSSM | 305 | 101 | 63 | 263 | 77.6% | 75.1% | 80.7% |
|  | 11/25 Rule | 392 | 14 | 208 | 118 | 69.7% | 96.5% | 36.2% |

Example 6

Evaluation of the Case Based Reasoning System Using Independent Data Sets

Since the similarity metric of the CBR algorithm was generated and fine-tuned based on the training set, the performance of the CBR system in other independent datasets was evaluated. A set of 152 commercial samples of mostly subtype B was used. The results are shown in Table 2. Additionally, the sensitivity, specificity, and overall concordance in this unseen dataset were evaluated with other algorithms investigated in this study: SVM, PSSM, and the 11/25 rule. The results are shown in Table 2. In this test, CBR outperformed all other methods in both sensitivity and overall accuracy, achieving a sensitivity of 86.7% compared to 80% for SVM, and 75.6% for PSSM. The sensitivity of the 11/25 rule remained very low, missing two thirds of the X4 tropic viruses.

TABLE 2

CBR performance with independent dataset;
comparison with SVM, PSSM, and 11/25 rule

|  | Prediction Method | TN | FP | FN | TP | Concordance | Spec. | Sens. |
|---|---|---|---|---|---|---|---|---|
| Unseen set N = 152 | CBR | 81 | 26 | 6 | 39 | 78.9% | 75.7% | 86.7% |
|  | SVM | 80 | 27 | 9 | 36 | 76.3% | 74.8% | 80% |
|  | PSSM | 81 | 26 | 11 | 34 | 75.7% | 75.7% | 75.6% |
|  | 11/25 Rule | 101 | 6 | 30 | 15 | 76.3% | 94.4% | 33.3% |

In order to examine the robustness of the CBR tool and the case library for tropism prediction in non-optimal conditions, a group of 128 Subtype C V3 sequences was used to test the tool's predictive power. The results are shown in Table 3. Given that the case library is comprised of predominantly subtype B samples, the CBR performed well with a specificity of 80.5%, sensitivity of 69.6% and an overall concordance of 76.6%. The CBR performance in this subtype C set also was evaluated with the same SVM and PSSM models, as well as the 11/25 rule. While the specificity of all these methods was very high (>96%), the sensitivity to detect X4 usage was inadequate, missing the majority of the X4 tropic samples in the dataset.

TABLE 3

CBR performance on subtype C dataset; comparison
with SVM, PSSM, and the 11/25 rule

|  | Prediction Method | TN | FP | FN | TP | Concordance | Spec. | Sens. |
|---|---|---|---|---|---|---|---|---|
| Subtype C N = 128 | CBR | 66 | 16 | 14 | 32 | 76.6% | 80.5% | 69.6% |
|  | SVM | 79 | 3 | 24 | 22 | 78.9% | 96.3% | 47.8% |
|  | PSSM | 79 | 3 | 35 | 11 | 70.3% | 96.3% | 23.9% |
|  | 11/25 Rule | 81 | 1 | 34 | 12 | 72.7% | 98.8% | 26.1% |

Example 7

Evaluation of the Case Based Reasoning System to Adapt to New Cases

To demonstrate the artificial intelligence capability of the CBR system, and the ease of learning from new experiences, the subtype C sequences from the previous example were added to the case library, and the LOOCV was performed. The results improved significantly as shown in Table 4, with a specificity of 84.1%, sensitivity of 73.9% and an overall concordance of 80.5%, a 6% increase.

TABLE 4

CBR performance on subtype C dataset when including
subtype C samples into the case library

|  | TN | FP | FN | TP | Concordance | Spec. | Sens. |
|---|---|---|---|---|---|---|---|
| Subtype C N = 128 | 69 | 13 | 12 | 34 | 80.5% | 84.1% | 73.9% |

Example 8

Comparison of the Case Based Reasoning System on Treatment Experienced or Naïve Samples The CBR system was analyzed to determine whether it is useful for both treatment-experienced and treatment-naïve samples. The results are shown in Table 5, demonstrating that sensitivity to detect X4 usage is lower in the early disease group compared to the treatment-experienced group.

TABLE 5

CBR performance Using Treatment-Experienced
or Treatment Naïve Viruses

| Viruses | TN | FP | FN | TP | Concordance | Spec. | Sens. |
|---|---|---|---|---|---|---|---|
| Experienced | 150 | 46 | 15 | 249 | 86.7% | 76.3% | 94.3% |
| Naive | 142 | 53 | 7 | 26 | 73.7% | 72.8% | 78.8% |

Example 9

Evaluation of the Case Based Reasoning System in Combination with Other Systems Finally, the feasibility and possible benefits of combining these bioinformatics methods (SVM, PSSM, and the 11/25 Rule) were evaluated. To allow a fair comparison between the methods, the same training set as the CBR system was used to generate the PSSM and SVM model. To construct the SVM, the V3 sequences were coded into a vector of length 35×22 containing 0 or 1 at each position to describe the amino acid composition. Counts of selected nucleotide and amino acid ambiguities were used as additional input parameters. The SVM model was trained using the libsvm implementation from the R package e1071. The cutoff for SVM decision values was set at the default value of 0. The PSSM model was developed according to the previously published method (Jensen et al, 2003, J. Virol. 77(24): 13376-88). The 11/25 rule was also applied on the datasets (De Jong et al., 1992, J. Virol. 66(11):6777-80), which is based on the presence of amino acids K or R at position 11, and R at position 25.

Figure 10:
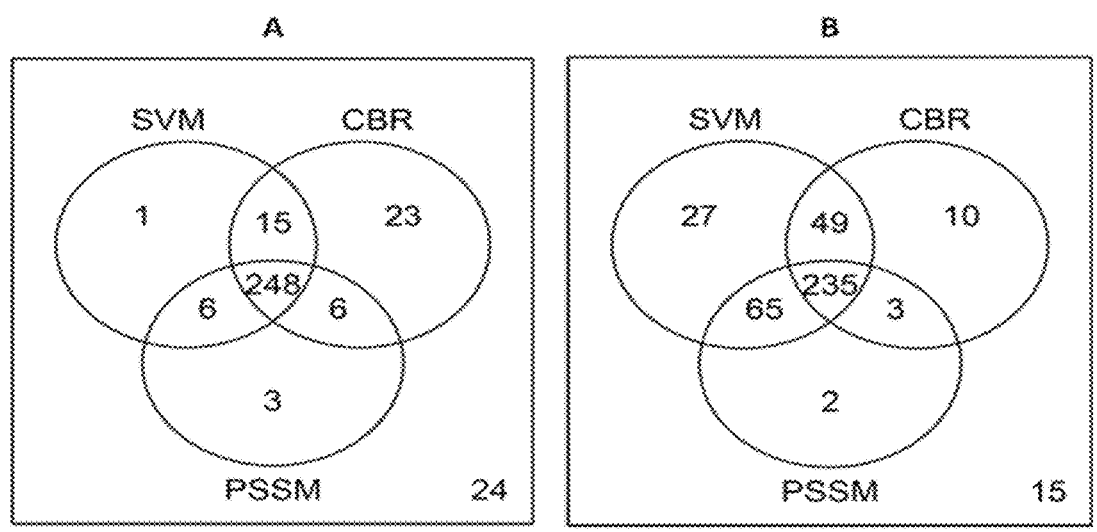
FIGS. 10A and 10B are Venn diagrams for tropism calls made by CBR, SVM, and PSSM models, showing that CBR was able to make tropism calls as well as or more accurately than the SVM or PSSM models.

Due to the poor performance of the 11/25 rule, only CBR, SVM, and PSSM were included in the analysis. The tropism predictions made by each method were used, and the true positive (X4 tropic) and negative (R5 tropic) calls were investigated in the form of a Venn diagram. FIG. 10A shows the calls made within X4 using (X4 or DM tropic) viruses, and 10B displays the predictions within R5 tropic subset (with tropisms determined by ESTA). As shown in FIG. 3A, among 326×4 using viruses there are 23 correctly called positive by solely CBR, compared to 1 by SVM and 3 by PSSM. In contrast, among 406 R5 viruses, 27 were correctly identified by SVM, and 2 by PSSM that were falsely called positive by CBR (FIG. 10B).

Example 10

Analysis of Utility of Case Based Reasoning Analysis of V3

A novel approach utilizing the case-based reasoning (CBR) technique to perform genotypic tropism prediction is described herein. The performance of several bioinformatics predictors commonly used as research tools or in the clinical practice were investigated. In the training set, CBR achieved a higher sensitivity (89.6%) than SVM (82.8%), PSSM (80.7%), or the 11/25 rule (36.2%), missing only 34 out of 326 total X4 using viruses. The specificity of the CBR tool (73.2%) was lower than SVM (92.6%) and the 11/25 rule (96.5%), but comparable to PSSM (75.1%). Since both the CBR adaptation strategy and PSSM cutoff were adjusted to have high X4 sensitivity, as a trade-off, these achieved lower specificity. Overall concordance for the CBR tool was 87.6% compared to 88.3% for SVM, 77.6% for PSSM, and 69.7% for the 11/25 rule. Since the number of R5 tropic samples was higher in the training set, and the SVM model was trained for highest accuracy in this dataset, it resulted in slightly lower overall concordance for CBR as compared to the SVM predictor. When these methods were evaluated in an independent dataset, sensitivity to detect X4 usage was significantly better for CBR (86.7%), compared to SVM (80%), PSSM (75.6%), and the 11/25 rule (33.3%), while specificity remained at a comparable level with the other methods. Since models such as SVM and PSSM are developed by generating a mathematical fit based on the training set, lower performance is achieved when the model is applied on unseen datasets. CBR has an advantage in that aspect since the knowledge base is stored as a set of cases with their solution, and it is therefore unnecessary for the information to be extracted into a different format where sub-optimal extrapolation may be performed.

CBR analysis of the V3 region offers several advantages over other bioinformatics methods used for genotype based tropism prediction. One main benefit is the ease of knowledge acquisition and modification. Existing databases of matched phenotype and genotype can be utilized as a case library. Maintenance of a CBR system is similar to editing a database. Cases that are no longer relevant or contain inaccurate information can be simply removed from the library, and new informative cases can be added. In contrast, in a rule-based or model-based approach, the rule set or the whole model must be strictly examined and/or re-developed in order to incorporate the new knowledge. Another benefit of the CBR algorithm is the capability to easily explain the solution. A particular tropism assessment can be justified by examining the identified similar V3 sequences and their degree of similarity to the query case. Diagnostic accuracy of CBR depends on the distribution of the study population stored in the case library, and can be improved by including a large spectrum of V3 sequences with diverse characteristics into the library. In the instant study, the accuracy of the algorithm for predicting tropism in a subtype C dataset improved by 6% when a set of samples with subtype C were added to the case library. Notably, and as previously reported (Eddy, 1998, Bioinformatics 14(9):755-63), other bioinformatics predictors have poor performance within subtype C samples, perhaps due to the fact that they were mostly derived using knowledge obtained from subtype B viruses.

The granularity of the tropism predictions made by the CBR, SVM, and PSSM algorithms was examined. Among 732 samples in the training set, 24 DM tropic viruses were found that none of the algorithms could correctly identify as X4-tropic. The X4 determination for these viruses may lie outside of the V3 loop. For the remaining cases, correct tropism predictions were made by each individual algorithm that were false negative or positive by others.

Different sites and amino acid substitutions in the V3 loop as well as additional physiochemical and sequence attributes were demonstrated to influence the coreceptor tropism differently. Mutations 7Y, 7K, 8I, 9K, 11R, and 30V were strongly associated with X4 usage (odds ratio>20, corrected p-value<0.05), as examined by Fisher's Exact test. Additionally, an increased number of amino acid and certain types of nucleotide mixtures (R, Y, W, and K) were found to occur significantly more in X4 using samples, in particular, within Dual/Mixed (DM) viruses. Peptide statistics extracted from the V3 sequence were evaluated, and increased total charge, isoelectric point, and basic values, as well as decreased value measured in the small grouping were significantly associated with X4 tropism. This information and the additional properties of the V3 loop were leveraged to better assess similarity in the context of tropism.

Case-based reasoning has been shown here to be a accurate and efficient genotypic tropism prediction tool. Improved sensitivity and specificity in independent datasets were observed when comparing CBR with other bioinformatics predictors, in particular, SVM, PSSM, and the 11/25 rule.

That which is claimed is:

1. A method for treating a patient having a human immunodeficiency virus 1 (HIV-1) infection based on the tropism of the HIV-1 present in a sample from the patient, comprising:
    (a) analyzing a biological sample obtained from a clinical patient to obtain an amino acid sequence, nucleic acid sequence, or both, of at least one portion of an envelope or envelope coding region of the viruses from the biological sample, wherein the at least one portion of the envelope or envelope coding region comprises the variable region 3 (V3) loop or coding region;
    (b) comparing the amino acid sequence, nucleic acid sequence, or both, of the at least one portion of the envelope or envelope coding region to sequence data stored in a database that comprises sequence and tropism data of a statistically significant number of viral isolates, wherein the comparing comprises a case based reasoning (CBR) analysis, and wherein the data comprises a plurality of sequences for the portion of the envelope or envelope coding region from viruses for which the tropism has been evaluated;
    (c) determining the tropism of the viruses from the biological sample based on the CBR analysis, wherein the tropism is X4 tropic, R5 tropic, or dual or mixed tropic (DM); and
    (d) treating the patient with an effective amount of an entry inhibitor based on the tropism determined in step (c).

2. The method of claim 1, wherein the clinical patient has been treated with a viral entry inhibitor.

3. The method of claim 2, wherein the viral entry inhibitor is PRO 542, TNX-355, mAb B12, mAb B4, BMS-488-403, UK-427857, SCH-D, GW-873140, AMD-3100, AMD-11070, TAK-220, TB-652, INCB9471, HGSI-004 Pro-140, mAb004, KRH-3140, or KRH-3955.

4. The method of claim 1, wherein the clinical patient has not been treated with a viral entry inhibitor.

5. The method of claim 1, wherein the data comprises a plurality of sequences from viruses of the same subtype as the viruses from the biological sample.

6. The method of claim 1, wherein the amino acid sequence of the at least one portion of the envelope is obtained.

7. The method of claim 1 further comprising:
    determining sequence characteristics of the amino acid sequence or nucleic acid sequence of the at least one portion of the envelope or envelope coding region, wherein the sequence characteristics are nucleotide or amino acid mixtures, molecular weight, net charge, isoelectric point, molar composition, profile Hidden Markov Model (pHMM) values, or a combination thereof; and
    comparing the sequence characteristics of the at least one portion of the envelope or envelope coding region to sequence characteristics stored in a database, wherein the comparing uses a case based reasoning (CBR) analysis, and wherein the data comprises a plurality of sequence characteristics from viruses for which the tropism has been evaluated.

8. A system for use in the method of claim 1, comprising:
    a computer readable medium; and
    a processor in communication with the computer readable medium, the processor configured to:
        receive sequence data, the sequence data representing an amino acid sequence, a nucleic acid sequence, or both of at least one portion of an envelope or envelope coding region of a human immunodeficiency virus 1 (HIV-1) from a biological sample obtained from a clinical patient, wherein the at least one portion of the envelope or envelope coding region comprises the variable region 3 (V3) loop or coding region;
        access other sequence data from HIV-1 viruses for which tropism has been evaluated;
        compare the received sequence data to the other sequence data;
        determine whether there is at least one sequence feature in the received sequence data; and
        in response to a determination that there is the at least one sequence feature in the received sequence data, determine the tropism of the virus from the biological sample using a case based reasoning analysis, wherein the tropism is X4 tropic, R5 tropic, or dual or mixed tropic (DM).

9. The system of claim 8, further comprising at least one database in communication with the processor, wherein the at least one database comprises the other sequence data.

10. The system of claim 9, wherein the at least one database further comprises data for the tropism of the viruses from which the other sequence data was obtained.

11. The system of claim 9, wherein the at least one database further comprises amino acid sequences, nucleic acid sequences, or both associated with a plurality of samples from clinical patients who have been exposed to an entry inhibitor.

12. The system of claim 9, wherein the at least one database further comprises amino acid sequences, nucleic acid sequences, or both from viruses of the same subtype as the virus from the biological sample.

13. The system of claim 8, wherein the clinical patient has been treated with a viral entry inhibitor.

14. The system of claim 8, wherein the processor is further configured to:
    receive sequence characteristics data, the sequence characteristics data representing nucleotide or amino acid mixtures, molecular weight, net charge, isoelectric point, molar composition, profile Hidden Markov Model (pHMM) values, or a combination thereof of the portion of at least one envelope or envelope coding region of the virus from the biological sample obtained from the clinical patient;
    access other sequence characteristics data from the viruses for which tropism has been evaluated;
    compare the received sequence characteristics data to the other sequence characteristics data from the viruses for which tropism has been evaluated;
    determine whether there is at least one distinct sequence characteristic in the received sequence characteristics data; and
    in response to a determination that there is the at least one distinct sequence characteristic in the received sequence characteristics data, determine the tropism of the virus from the biological sample using a case based reasoning analysis.

15. A non-transitory computer readable medium for use in the method of claim 1, comprising program code comprising:
    program code for receiving sequence data, the sequence data representing an amino acid sequence, nucleic acid sequence, or both of at least a portion of an envelope or envelope coding region of a human immunodeficiency virus 1 (HIV-1) from a biological sample obtained from a clinical patient, wherein the at least one portion of the envelope or envelope coding region comprises the variable region 3 (V3) loop or coding region;

program code for accessing other sequence data from HIV-1 viruses for which tropism has been evaluated;

program code for comparing the received sequence data to the other sequence data;

program code for determining whether there is at least one sequence feature in the received sequence data; and program code for, in response to a determination that there is the at least one sequence feature in the received sequence data, determining the tropism of the virus from the biological sample using a case based reasoning analysis, wherein the tropism is X4 tropic, R5 tropic, or dual or mixed tropic (DM).

16. The non-transitory computer readable medium of claim 15, wherein the other sequence data comprises amino acid sequences, nucleic acid sequences, or both associated with a plurality of samples from clinical patients who have been exposed to an entry inhibitor.

17. The non-transitory computer readable medium of claim 15, wherein the other sequence data comprises amino acid sequences, nucleic acid sequences, or both from viruses of the same subtype as the virus from the biological sample.

18. The non-transitory computer readable medium of claim 15, wherein the clinical patient has been treated with a viral entry inhibitor.

19. The non-transitory computer readable medium of claim 15, further comprising:

program code for receiving sequence characteristics data, the sequence characteristics data representing nucleotide or amino acid mixtures, molecular weight, net charge, isoelectric point, molar composition, profile Hidden Markov Model (pHMM) values, or a combination thereof of the portion of at least one envelope or envelope coding region of the virus from the biological sample obtained from the clinical patient;

program code for accessing other sequence characteristics data from viruses for which tropism has been evaluated;

program code for comparing the received sequence characteristics data to the other sequence characteristics data from the viruses for which tropism has been evaluated;

program code for determining whether there is at least one distinctive sequence characteristic in the received sequence characteristics data; and program code for, in response to a determination that there is the at least one distinctive sequence characteristic in the received sequence characteristics data, determining the tropism of the virus from the biological sample using a case based reasoning analysis.

* * * * *